(12) United States Patent
Zwier et al.

(10) Patent No.: US 8,999,653 B2
(45) Date of Patent: Apr. 7, 2015

(54) METHOD FOR DETECTING MEMBRANE PROTEIN INTERNALIZATION

(75) Inventors: Jurriaan Zwier, Rochefort du Gard (FR); Robert Poole, Ringwood Hampshire (GB); Herve Ansanay, Montpellier (FR); Michel Fink, Bagnols sur Ceze (FR); Eric Trinquet, Pont Saint Esprit (FR)

(73) Assignee: Cis-Bio International, Gif sur Yvette Cedex (FR)

( * ) Notice: Subject to any disclaimer, the term of this patent is extended or adjusted under 35 U.S.C. 154(b) by 684 days.

(21) Appl. No.: 13/056,738

(22) PCT Filed: Jul. 30, 2009

(86) PCT No.: PCT/FR2009/051538
§ 371 (c)(1),
(2), (4) Date: May 31, 2011

(87) PCT Pub. No.: WO2010/012962
PCT Pub. Date: Feb. 4, 2010

(65) Prior Publication Data
US 2012/0009599 A1    Jan. 12, 2012

(30) Foreign Application Priority Data
Jul. 31, 2008  (FR) .................................. 08 55296

(51) Int. Cl.
| | |
|---|---|
| *G01N 33/53* | (2006.01) |
| *C12Q 1/00* | (2006.01) |
| *G01N 21/76* | (2006.01) |
| *G01N 33/542* | (2006.01) |
| *G01N 33/50* | (2006.01) |
| *G01N 33/58* | (2006.01) |

(52) U.S. Cl.
CPC .......... *G01N 33/542* (2013.01); *G01N 33/5035* (2013.01); *G01N 33/58* (2013.01); *G01N 2458/40* (2013.01)

(58) Field of Classification Search
USPC ................ 435/2, 3, 6, 7.2, 15, 441, 444, 326, 435/320.1, 374, 159, 4, 29, 183, 195; 436/517, 56, 63, 81, 171, 172
See application file for complete search history.

(56) References Cited

U.S. PATENT DOCUMENTS

| | | |
|---|---|---|
| 4,637,988 A | 1/1987 | Hinshaw et al. |
| 4,670,572 A | 6/1987 | Hinshaw et al. |
| 4,761,481 A | 8/1988 | Hale et al. |
| 4,794,191 A | 12/1988 | Hinshaw et al. |
| 4,801,722 A | 1/1989 | Hinshaw et al. |
| 4,837,169 A | 6/1989 | Toner |
| 4,859,777 A | 8/1989 | Toner |
| 4,927,923 A | 5/1990 | Mathis et al. |
| 5,032,677 A | 7/1991 | Hale et al. |
| 5,055,578 A | 10/1991 | Hale et al. |
| 5,106,957 A | 4/1992 | Hale et al. |
| 5,116,989 A | 5/1992 | Hale et al. |
| 5,202,423 A | 4/1993 | Kankare et al. |
| 5,316,909 A | 5/1994 | Xu |
| 5,324,825 A | 6/1994 | Kankare et al. |
| 5,622,821 A | 4/1997 | Selvin et al. |
| 8,470,523 B2 * | 6/2013 | Pribilla et al. ..................... 435/4 |
| 2005/0026234 A1 | 2/2005 | Violin et al. |
| 2010/0184107 A1* | 7/2010 | Lefkowitz et al. .............. 435/15 |

FOREIGN PATENT DOCUMENTS

| | | |
|---|---|---|
| EP | 0180492 A1 | 5/1986 |
| EP | 0321353 A1 | 6/1989 |
| GB | 2 223 096 A | 3/1990 |
| WO | WO 90/00550 A1 | 1/1990 |
| WO | WO 93/05049 A1 | 3/1993 |
| WO | WO 98/55635 A1 | 12/1998 |
| WO | WO 00/03246 A2 | 1/2000 |
| WO | WO 00/48990 A1 | 8/2000 |

(Continued)

OTHER PUBLICATIONS

Maurel et al. Cell surface detection of mernbra.ne protein interaction with homogeneous time-resolved fluorescence resonance energy transfer technology, Analytical Biochemistry 329: 253-262 (2004).*

(Continued)

*Primary Examiner* — Gail R Gabel

(74) *Attorney, Agent, or Firm* — Millen, White, Zelano & Branigan, P.C.

(57) ABSTRACT

The instant invention provides for methods for detecting the internalization of a transmembrane protein of interest expressed at the surface of a cell. More specifically, the methods involve (a) labelling the protein of interest with a fluorescent metal complex, the lifetime of which is greater than 0.1 ms, (b) adding to the reaction medium a composition capable of causing the internalization of the protein of interest, (c) adding to the reaction medium (1) a modulating agent which is a fluorescent FRET acceptor compound compatible with the fluorescent metal complex, the final concentration of which in the reaction medium is greater than $10^{-7}$M; or (2) a reducing agent, the redox potential of which is less than +0.1 V and preferably between 0.25 and 0.75 V; or (3) an agent which binds specifically, by non-covalent bonding, with the fluorescent metal complex; (d) adding a metal ion which competes with the rare earth so as to form a non-fluorescent metal complex; (d) measuring the luminescence emitted by the reaction medium at the emission wavelength of the fluorescent metal complex and/or at the emission wavelength of the modulating compound when the compound is a fluorescent acceptor compound; and (e) comparing the signal measured in step d) with a reference signal measured on cells having been subjected only to steps a) and c).

36 Claims, 4 Drawing Sheets

(56) References Cited

FOREIGN PATENT DOCUMENTS

| | | |
|---|---|---|
| WO | WO 00/48991 A1 | 8/2000 |
| WO | WO 00/75237 A2 | 12/2000 |
| WO | WO 01/58923 A2 | 8/2001 |
| WO | WO 01/59451 A1 | 8/2001 |
| WO | WO 01/67106 A2 | 9/2001 |
| WO | WO 01/96877 A2 | 12/2001 |
| WO | WO 2004/065963 A2 | 8/2004 |
| WO | WO 2004/072232 A2 | 8/2004 |
| WO | WO 2005/007822 A2 | 1/2005 |
| WO | WO 2007/116069 A1 | 10/2007 |
| WO | WO 2008/007089 A1 | 1/2008 |
| WO | WO 2008/063721 A2 | 5/2008 |
| WO | WO 2008/103393 A1 | 8/2008 |
| WO | WO 2009/010580 A1 | 1/2009 |

OTHER PUBLICATIONS

Handl et al. Lanthanide-based luminescent assays for ligand-receptor interactions, Life Sciences 77: 361-371 (2005).*

Mathis. Probing Molecular Interactions with Homogeneous Techniques Based on Rare Earth Cryptates and Fluorescence Energy Transfer. Clin. Chem. 41 (9): 1391-1397 (1995).*

Juillerat et al. Directed Evolution of O6-Alkylguanine-DNA Alkyltransferase for Efficient Labeling of Fusion Proteins with Small Molecules In Vivo. Chemistry and Biology 10: 313-317 (Apr. 2003).*

Maurel et al. Cell surface detection of mernbrane protein interaction with homogeneous time-resolved fluorescence resonance energy transfer technology, Analytical Biochemistry 329: 253-262 (2004).*

International Search Report of PCT/FR2009/051538 (Jan. 26, 2010).

D. D. Thomas et al., "Fluorescence Energy Transfer in the Rapid-Diffusion Limit", Proc. Natl. Acad. Sci., vol. 75, No. 12 (Dec. 1978) pp. 5746-5750.

R. A. Poole et al., "Synthesis and Characterisation of Highly Emissive and Kinetically Stable Lanthanide Complexes Suitable for Usage 'in cellulo'", Org. Biomol. Chem., vol. 3 (2005) pp. 1013-1024.

C. M. McCann et al., "Peptide Tags for Labeling Membrane Proteins in Live Cells with Multiple Fluorophores", BioTechniques, vol. 38, No. 6 (2005) pp. 945-952.

G. Mathis, "Probing Molecular Interactions with Homogeneous Techniques Based on Rare Earth Cryptates and Fluorescence Energy Transfer", Clin. Chem., vol. 41, No. 9 (1995) pp. 1391-1397.

A. Juillerat et al., "Directed Evolution of $O_6$-Alkylguanine-DNA Alkyltransferase for Efficient Labeling of Fusion Proteins with Small Molecules In Vivo", Chemistry & Biology, vol. 10 (Apr. 2003) pp. 313-317.

A. Gautier et al., "An Engineered Protein Tag for Multiprotein Labeling in Living Cells", Chemistry & Biology, vol. 15 (Feb. 2008) pp. 128-136.

T. Gronemeyer et al., "Directed Evolution of $O_6$-Alkylguanine-DNA Alkyltransferase for Applications in Protein Labeling", Protein Engineering, Design & Selection, vol. 19, Nol. 7 (2006) pp. 309-316.

R. R. Gainetdinov et al., "Desensitization of G Protein-Coupled Receptors and Neuronal Functions", Annu. Rev. Neurosci., vol. 27 (2004) pp. 107-144.

Q. Zheng et al., "A New Class of Macrocyclic Lanthanide Complexes for Cell Labeling and Magnetic Resonance Imaging Applications", J. Am. Chem. Soc., vol. 127 (2005) pp. 16178-16188.

B. Albert Griffin et al., "Specific Covalent Labeling of Recombinant Protein Molecules Inside Live Cells", Science, vol. 281 (Jul. 10, 1998) pp. 269-272.

P. G. Charest et al., "Monitoring Agonist-Promoted Conformational Changes of Beta-Arrestin in Living Cells by Intramolecular BRET", European Molecular Biology Organization Reports, vol. 6, No. 4 (2005) pp. 334-340.

F. Kielar et al., "A Mechanistic Study of the Dynamic Quenching of the Excited State of Europium(III) and Terbium(III) Macrocyclic Complexes by Charge- or Electron Transfer", Org. Biomol. Chem., vol. 5 (2007) pp. 2975-2982.

N. George et al., "Specific Labeling of Cell Surface Proteins with Chemically Diverse Compounds", J. Am. Chem. Soc., vol. 126 (2004) pp. 8896-8897.

S. R. Adams et al., "New Biarsenical Ligands and Tetracysteine Motifs for Protein Labeling in Vitro and in Vivo: Synthesis and Biological Applications", J. Am. Chem. Soc., vol. 124 (2002) pp. 6063-6076.

D. D. Root, "In Situ Molecular Association of Dystrophin with Actin Revealed by Sensitized Emission Immuno-Resonance Energy Transfer", Proc. Natl. Acad. Sci., vol. 94 (May 1997) pp. 5685-5690.

B. J. Reaves et al., "The Effect of Wortmannin on the Localisation of Lysosomal Type I Integral Membrane Glycoproteins Suggests a Role for Phosphoinositide 3-Kinase Activity in Regulating Membrane Traffic Late in the Endocytic Pathway", Journal of Cell Science, vol. 109 (1996) pp. 749-762.

D. Maurel et al., "Cell Surface Detection of Membrane Protein Interaction with Homogeneous Time-Resolved Fluorescence Resonance Energy Transfer Technology", Analytical Biochemistry, vol. 329 (2004) pp. 253-262.

P. Dhonukshe et al., "Clathrin-Mediated Constitutive Endocytosis of PIN Auxin Efflux Carriers in *Arabidopsis*", Current Biology, vol. 17 (Mar. 20, 2007) pp. 520-527.

English Abstract of EP0321353, publication date Jun. 21, 1989.
English Abstract of EP0180492, publication date May 7, 1986.
English Translation of EP 0321353, publication date Jun. 21, 1989.

* cited by examiner

METHOD FOR DETECTING MEMBRANE PROTEIN INTERNALIZATION

The invention relates to a method for detecting membrane protein internalization by living cells and is particularly useful for demonstrating compounds capable of causing this internalization. More specifically, the present invention describes a method for detecting the internalization of a transmembrane protein coupled to a fluorescent metal complex, based on measuring a variation in the luminescence of said fluorescent metal complex when it is internalized.

PRIOR ART

Internalization:

During the activation of cells by ligands of membrane receptors, the latter are subjected to a cascade of mechanisms which conventionally results in the internalization by the cell. This process firstly makes it possible to suppress or decrease the stimulus undergone by the cell owing to the uptake of the ligand, generally an agonist, and secondly results in desensitization of the receptors and therefore an interruption of the conventional signal transduction cascade. This desensitization of the transduction unit is a complex mechanism which has been relatively well described (see, for example, Gainetdinov et al., Annu Review Neurosci 2004 v27 p 107-44).

This internalization mechanism is one of the major processes for regulating G-protein coupled receptors (GPCRs) and also receptor tyrosine kinases.

Schematically, the activation of a GPCR by an agonist results in phosphorylation of this receptor in its intracellular part, thereby inducing the recruitment of a certain number of intracellular proteins, in particular of arrestin which causes the formation of clathrin-coated endocytotic vesicles. These vesicles are then dealt with by intracellular transport mechanisms which result in their degradation by fusion with lyzosomes, or else in their reconversion by fusion with the plasma membrane.

GPCRs constitute a target of choice for the development of new molecules with therapeutic activity, and several techniques exist for measuring variations in their level of activation by candidate compounds: agonists, antagonists or else inverse agonists. Some of them actually have the objective of detecting the activation of GPCRs by studying events linked to the internalization thereof.

Arrestin is an intracellular protein which plays a major role in the GPCR internalization process and it is used in several approaches for detecting internalization, as shown by the documents hereinafter.

Application WO 01/67106 describes a method which aims to identify GPCR ligands by measuring the modulation of the binding between a GPCR and a constitutively active mutant of arrestin, the activity of which is dependent on the level of phosphorylation of the GPCR, said ligand being labeled with a radioactive atom, an enzyme, a reporter protein or a fluorescent compound.

Application WO 01/59451 describes a method for detecting the activation of a GPCR which uses the "ICAST" technology (Intercistronic Complementary Analysis Screening technology) based on the complementation of two sub-units of a mutant enzyme, each fragment of the enzyme being expressed in the form of a fusion protein with, on the one hand, a GPCR and, on the other hand, arrestin for example. If a GPCR-arrestin interaction takes place, the enzyme will be reconstituted by complementation and will be able to generate a detectable signal. Here again, it is therefore a question of analyzing the activation of GPCRs by detection of the binding thereof to arrestin. This technique can be improved by using mutants of GPCR or of arrestin, as described in application WO 01/58923.

Application WO 2005/007822 describes a method for determining whether a compound modulates the interaction between two proteins of interest. This method is also based on the detection of GPCR-arrestin binding. The method presented is based on the use of a GPCR fused, in its C-terminal part, with a transcription factor via a peptide sequence sensitive to a specific protease. The arrestin is, for its part, fused with this protease. During the activation of the GPCR by an agonist ligand, the arrestin will interact with the GPCR, which will have the effect of bringing the protease close to the cleavage sequence and of causing the release of the transcription factor, which will then be capable of activating the transcription of a reporter gene, the activity of which may be detected.

One of the problems associated with the use of arrestin-GPCR binding as a marker for the activation of a GPCR is the unstable nature of this binding, which is only an intermediate step in a cascade of events resulting in the formation of endocytotic vesicles. Application WO 04/065963 addresses this problem by using arrestin mutants which, unlike wild-type arrestin, are not capable of binding with the protein partners of this cascade and, consequently, remain relatively stably bound to the receptor.

Charest et al. (*EMBO Rep.* 2005 April; 6(4):334-40) have developed a technique for detecting variation in the three-dimensional structure of arrestin, which occurs during the interaction thereof with activated GPCRs; the authors have constructed a luciferase-arrestin-YFP (yellow fluorescent protein) fusion protein and have demonstrate an increase in the intramolecular BRET (Bioluminescent Resonance Energy Transfer) signal during the activation of GPCRs (technique known as "double-brilliance arrestin").

The company Molecular Devices markets the "Transfluor®" technology, described in particular in patent EP 1 015 608, which is based on the use of an arrestin-GFP fusion protein: the use of cells expressing this fusion protein makes it possible to visualize, with the appropriate image acquisition equipment, the translocation of arrestin-GFP and the redistribution thereof, in the cell, in response to the activation of a GPCR of interest.

Other approaches for demonstrating membrane receptor internalization which are not based on the detection of GPCR-arrestin binding or intracellular translocation of arrestin have been described in particular in the documents hereinafter.

Application WO 00/03246 describes a method for identifying compounds capable of inducing GPCR internalization, based on luminescent labeling of the receptors, either using a GPCR-luminescent protein fusion protein, or by adding to the medium a labeled molecule capable of binding to these receptors. This method comprises a step for acquisition of images of the cells which must be analyzed in order to identify those of which the receptors have been internalized.

The company Amersham Biosciences markets cyanin derivatives under the trade name CypHer5®; these organic fluorophores, described in particular in application WO 00/75237, have the property of being only very weakly fluorescent at neutral pH, and very fluorescent at acid pH. These cyanin derivatives can be conjugated, for example, with antibodies capable of binding to GPCRs: during the internalization of the antibody-Cypher5 bound to the GPCRs, Cypher5 will go from a medium at neutral pH (extracellular medium) to a medium at acid pH (endosome) and its luminescence will increase.

Lanthanide Complexes and Fluorescence Quenching by Dynamic Fret

The use of lanthanide complexes (also hereinafter referred to as "rare earth complexes") as fluorescent compounds useful for studying biological phenomena was developed in the 1990s (see, for example, the article by Mathis et al., Clin. Chem. 1995 September; 41(9):1391-7).

The FRET phenomenon is widely used in biology, in particular for studying biological interactions. It is based on the use of a fluorescent donor compound (for example a lanthanide complex) and an optionally fluorescent acceptor compound, each coupled to a biological molecule. When a studied biological interaction causes the biological molecules to become closer to one another, and the donor compound is excited, energy transfer takes place between the donor and the acceptor and will result in a variation in the luminescence emitted by the reaction medium. Several companies market reagents for carrying out this approach in order to study biological processes; for example, the applicant provides donor and acceptor compounds and also kits for studying particular biological phenomena (detection of enzymatic activity, assaying of second messengers, etc.).

The phenomenon of dynamic energy transfer between two donor and acceptor compounds freely diffusing in solution in a medium has been described in particular by D. Thomas et al., (1978), PNAS, 75: 12, 5746-5750. This phenomenon is often denoted by the acronym DEFET, which means "Diffusion Enhanced Fluorescence Energy Transfer". Unlike the energy transfer conventionally used to study biological phenomena, which is based on the occurrence of a biological interaction that will bring the donor and acceptor compounds closer to one another, FRET by dynamic transfer, or DEFET, is based on the free diffusion of one or of both of the FRET partners in the reaction medium.

D. Thomas et al. (1978), PNAS, 75: 12, 5746-5750 have described a DEFET between a terbium complex ($Tb(DPA)_3$) and rhodamine, both in solution, and have also used DEFET to determine the distance of closest approach between $Tb(DPA)_3$ present in the aqueous medium of a membrane vesicle and the eosin chromophore of eosin-phosphatidylcholine contained in the membrane. These studies were carried out under "rapid diffusion limit" conditions, in particular using a donor fluorophore with a long lifetime (2.2 msec). These conditions, in which the efficiency of the energy transfer depends essentially only on the distance of closest approach between the donor and the acceptor, make it possible in particular to observe a signal at low acceptor concentration.

Patent application GB 2 223 096 describes a method for detecting a molecule (for example an antibody or an antigen) which is based on the very concept of dynamic FRET, which is known to depend on the diffusion constant of the FRET partners. The method described in fact consists in measuring the variation in dynamic FRET between a donor compound and an acceptor compound, this variation resulting from the modification of the diffusion of the donor or of the acceptor in the medium following its interaction with the molecule to be detected. This method requires that one of the donor or acceptor compounds be conjugated with an entity capable of interacting with the molecule to be detected (for example, the donor or the acceptor is conjugated with a protein or an antibody).

Zheng et al. (J. Am. Chem. Soc. 2005, 127, 16178-16188) have developed a class of lipophilic macrocycles (DTPA-PDA-$C_n$, n=10,12) capable of complexing lanthanides and of being nonspecifically inserted into lipid membranes, for cell labeling applications and applications for use in nuclear magnetic resonance (in the case of gadolinium complexes). The authors used the DEFET technique to determine the cellular localization of these complexes, by measuring the signal resulting from energy transfer between terbium complexes and calcein. The authors were able to detect a DEFET between their complexes and calcein when said calcein is added to the extracellular medium (calcein is cell-membrane-impermeable), but not with intracellular calcein (introduced into the cells in the form of a neutral ester of calcein), and therefore concluded therefrom that their lipid lanthanide complexes are inserted on the external face of the plasma membrane. This team did not study the possible variations in signal in the event of internalization of their lanthanide complexes.

DEFET has also been used by several teams in order to study the structure of proteins incorporating energy-acceptor motifs and the interaction thereof with energy-donor compounds, in order to determine the electrostatic potentials at the surface of proteins.

Lanthanide Complexes and Fluorescence Quenching by Redox Effect

The effect of certain reducing agents on the luminescence of lanthanide complexes has been described in the literature:

Kielar et al., for example, have studied the dynamic quenching of the excited state of europium and terbium complexes by various reducing agents (Org. Biomol. Chem., 2007, 5, 2975-2982), and have shown that, for the rare earth complexes studied, the compounds having an oxidation potential slightly lower than 1 V can have a fluorescence-quenching effect by reduction; this is the case, for example, of the iodide ion (+0.54 V), of urate (+0.59 V), ascorbate (+0.30 V) and certain catecholates (+0.54 V at pH 7). These authors have, moreover, demonstrated that the fluorescence-quenching effect of these compounds on terbium complexes is greater than that observed on europium complexes, having an identical chelating structure.

Application WO 2008/007089 relates to a method for assaying analytes having a reducing capacity by means of terbium or europium complexes.

A real need exists for a method which is sensitive, easy to implement and suitable for a high-throughput application, for detecting the internalization of membrane proteins of interest. Such a method would be particularly advantageous for easily demonstrating compounds capable of causing membrane protein internalization, in particular in approaches aimed at detecting novel medicaments. Moreover, since only 10 to 40% of the receptors capable of being internalized are actually internalized, the method in question should be sufficiently sensitive to allow the observation of a variation of signal when internalization takes place.

DEFINITIONS

"FRET acceptor compound compatible with a fluorescent metal complex": this expression denotes a FRET acceptor compound which forms a pair of FRET partners with said fluorescent metal complex.

"Pair of FRET partners": this expression denotes a pair consisting of a donor fluorescent compound and an acceptor compound; when they are in proximity to one another and when they are excited at the excitation wavelength of the donor fluorescent compound, these compounds emit a FRET signal. It is known that, in order for two fluorescent compounds to be FRET partners, the emission spectrum of the donor fluorescent compound must partially overlap the excitation spectrum of the acceptor compound. The preferred FRET-partner pairs are those for which the value R0 (Förster distance, distance at which energy transfer is 50% efficient) is greater than or equal to 30 Å.

"FRET signal": denotes any measurable signal representative of a FRET between a donor fluorescent compound and an acceptor compound. A FRET signal can therefore be a variation in the intensity or in the lifetime of luminescence of the donor fluorescent compound or of the acceptor compound when the latter is fluorescent.

"Reaction medium": denotes any container in which living cells can be brought into contact with reagents, such as, for example, a well of a plate, a test tube, etc.

"EDTA": ethylenediaminetetraacetic acid;
"DTPA": diethylenetriaminepentaacetic acid;
"TTHA": triethylenetetramine-N,N,N',N'',N''',N'''-hexaacetic acid;
"DOTA": 1,4,7,10-tetraazacyclododecane-N,N',N'',N'''-tetraacetic acid;
"NTA": nitrilotriacetic acid;
"HDTA": hexamethylenediaminetetraacetic acid;
"DTPP": diethylenetriaminepentaphosphonic acid;
"EDTP": ethylenedinitrilotetrakis(methylphosphonic) acid;
"NTP": nitrilotri(methylenephosphonic) acid;
"DOTP": 1,4,7,10-tetraazacyclododecane-N',N'',N''',N''''-tetrakis(methylenephosphonic) acid;
"DO3A": 1,4,7,10-tetraazacyclododecanetrisacetic acid;
"DOTAGA": 1-(1-carboxy-3-carboxypropyl)-4,7,10-(carboxymethyl)-1,4,7,10-tetraazacyclododecane;
"DY647": fluorophore with a pentamethine structure sold by the company Dyomics;
"D2": organic fluorescent acceptor compound marketed by the company Cisbio Bioassay;
"PBS": phosphate buffer solution;
"Lumi4-Tb": terbium complex marketed by the companies Lumiphore and Cisbio Bioassay;
"DMEM": "Dulbecco's Modified Eagle's Medium", cell culture medium, commercially available and used in many applications;
"NHS": N-hydroxysuccinimide.

DESCRIPTION

The subject of the present invention is a method for detecting protein internalization, which comprises the following steps:
a) labeling the protein of interest with a fluorescent metal complex comprising a lanthanide or ruthenium, the lifetime of which is greater than 0.1 ms, preferably between 0.5 and 6 ms;
b) adding to the reaction medium a compound capable of causing the internalization of the protein of interest;
c) adding to the reaction medium a modulating agent selected from:
  1. a fluorescent or nonfluorescent FRET acceptor compound compatible with said fluorescent metal complex, the final concentration of which in the reaction medium is greater than $10^{-7}$ M, and preferably between $10^{-6}$ M and $10^{-3}$ M, and the molecular weight of which is less than 50 kD, preferably between 0.1 and 10 kD;
  2. a reducing agent, the redox, potential of which is less than +0.1 V and preferably between 0.25 and 0.75 V;
  3. an agent which binds specifically, by noncovalent bonding, with the to fluorescent metal complex;
  4. a metal ion which competes with the lanthanide or the ruthenium so as to form a nonfluorescent metal complex;
d) measuring the luminescence emitted by the reaction medium at the emission wavelength of the fluorescent metal complex and/or at the emission wavelength of the modulating agent;
e) comparing the signal measured in step d) with a reference signal measured on cells having been subjected only to steps a) and c), a difference in the signal measured in step d) compared with the reference signal being representative of the internalization of the protein of interest.

These essential steps can be carried out in this order (a, b, c, d, e). This embodiment is preferred since, in this case, the modulating compound is not present in the extracellular medium during the internalization of the protein of interest, thereby reducing the risk of the modulating compound being present in the endosomes.

When the modulator is a FRET acceptor compound, which is the case in the preferred embodiment of the invention, or a reducing agent, these steps can also be carried out in the following order: a), c), b), d), e).

Moreover, a washing step can be added between step a) and the following step. The term "washing step" is intended to mean a step consisting in changing the culture medium, one or more times (preferably 2 or 3 times). This washing step serves to remove from the extracellular medium the fluorescent metal complex that is not coupled with the protein of interest; this step is nevertheless optional since the invention is based on the observation of a difference in signal according to internalization. However, it is preferable to carry out this washing in order to improve the sensitivity of the method.

The method according to the invention is based on the detection of a signal emitted by a reaction medium containing living cells and the appropriate reagents, and the intensity of which varies according to the internalization, by the cells, of a membrane protein of interest.

More specifically, in the method according to the invention, the membrane protein of interest is bound, directly or indirectly and at the level of a domain exposed to the extracellular medium, to a fluorescent metal complex capable of emitting a luminescent signal. The extracellular medium contains a compound (termed "modulating compound"), the presence of which in the reaction medium has the effect of modifying the signal emitted by the fluorescent metal complex.

The internalization of the membrane protein of interest modifies the accessibility of the fluorescent metal complex for the modulating compound: the fluorescent metal complex will no longer be exposed to the extracellular medium, but to that of the inside of an endocytotic vesicle, or to the cytosol after a certain period of time. The inventors have found that this change in accessibility of the fluorescent metal complex for the modulating compound results in a variation in the luminescence signal emitted by the reaction medium, this variation being detectable or even optionally quantifiable, despite the fact that only 10 to 40% of the transmembrane receptors capable of being internalized actually are internalized.

The luminescence signal emitted by the reaction medium corresponds to the luminescence emitted by the fluorescent metal complex or else, when the modulator is a FRET acceptor compound, to that emitted by the modulator.

In both cases it is the difference in accessibility of the fluorescent metal complex for the modulating compound which leads to a difference in the luminescence measured in the reaction medium.

The reagents used in the method according to the invention and also the variants of implementation thereof will now be described in greater detail.

A. Fluorescent Metal Complex

In general, the expression "fluorescent metal complex" is intended to mean a compound consisting of a lanthanide or of ruthenium and a polydentate complexing agent, i.e. an agent comprising at least 2, and preferably between 2 and 9, electron-donor heteroatoms, such as N, O or S, these atoms forming coordination bonds with the lanthanide or the ruthenium. Preferably, the fluorescent metal complex comprises one or more chromophores consisting of aromatic structures; preferably, these aromatic structures comprise 1, 2 or 3 heteroatoms selected from N and O, which play the role of lanthanide or ruthenium coordination atoms.

A fluorescent metal complex suitable for the purposes of the invention should be stable in terms of association/dissociation of the complexing agent and the rare earth, and its formation constant (Kf) should preferably be greater than $10^{10} M^{-1}$.

Many complexing agents have been described and are known to those skilled in the art: by way of examples of complexing agents, mention may be made of the following compounds: EDTA, DTPA, TTHA, DOTA, NTA, HDTA, DTPP, EDTP, HDTP, NTP, DOTP, DO3A, DOTAGA.

Examples of fluorescent metal complexes suitable for the purposes of the invention are:

Lanthanide cryptates comprising one or more pyridine units. Such rare earth cryptates are described, for example, in patents EP 0 180 492, EP 0 321 353 and EP 0 601 113 and in international application WO 01/96 877. Cryptates of terbium (Tb3+) and of europium (Eu3+) are particularly suitable for the purposes of the present invention. Lanthanide cryptates are marketed by the company Cisbio Bioassay. By way of nonlimiting examples, mention may be made of the europium cryptates having the formulae below, which can be coupled to the compound to be labeled by a reactive group, such as the NHS group or a reactive group R.

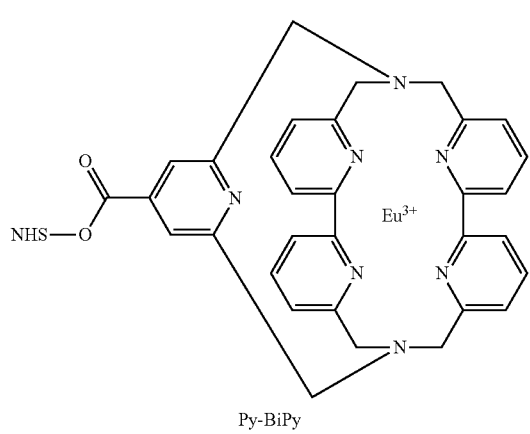

Py-BiPy

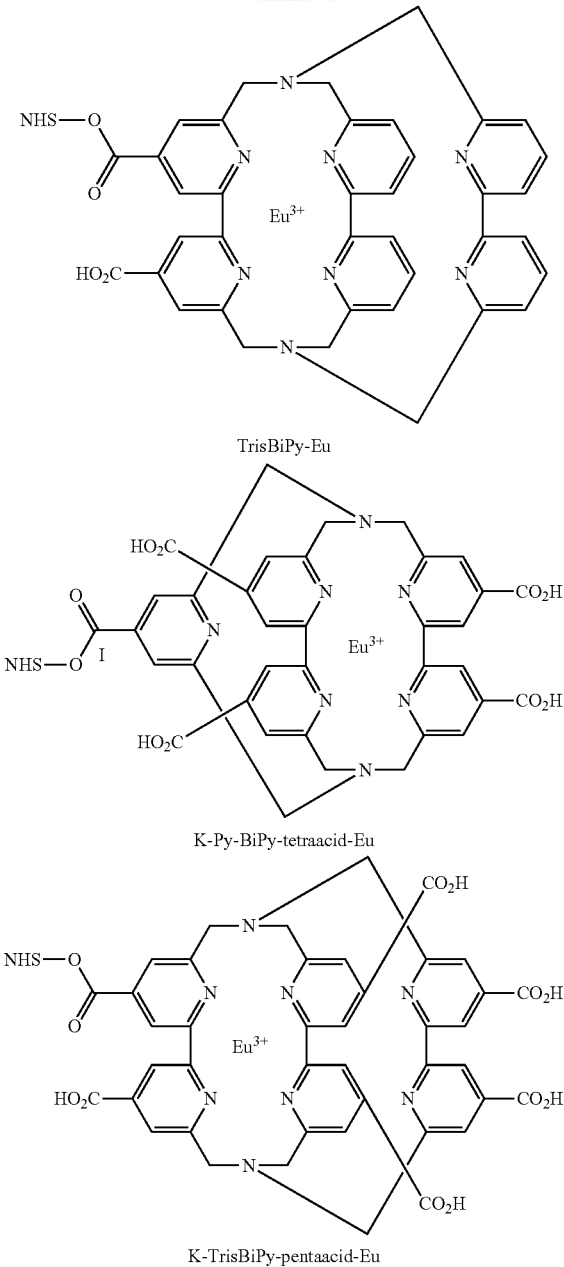

TrisBiPy-Eu

K-Py-BiPy-tetraacid-Eu

K-TrisBiPy-pentaacid-Eu

Lanthanide chelates, described in particular in U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169, U.S. Pat. No. 4,859,777. Patents EP 0 403 593, U.S. Pat. No. 5,324,825, U.S. Pat. No. 5,202,423 and U.S. Pat. No. 5,316,909 describe chelates composed of a nonadentate ligand such as terpyridine. Lanthanide chelates are marketed by the company PerkinElmer.

Lanthanide complexes consisting of a chelating agent such as tetraazacyclododecane, substituted with a chromophore comprising aromatic rings, such as those described by Poole R. et al. in Biomol. Chem, 2005, 3, 1013-1024 "Synthesis and characterisation of highly emissive and kinetically stable lanthanide complexes suitable for usage in cellulo", can also be used. The complexes described in application WO2009/10580 can also be used.

The rare earth cryptates described in patents EP 1 154 991 and EP 1 154 990 can also be used.

The terbium cryptate Lumi4-Tb from the company Lumiphore, marketed by Cisbio bioassays.

The terbium cryptate Tb(KR) having the formula below (which can be coupled to the compound to be labeled by a reactive group, in this case, for example, an NHS group):

Ruthenium chelates, in particular complexes consisting of a ruthenium ion and several bipyridines, such as ruthenium(II) tris(2,2'-bipyridine).

The terbium chelate DTPA-cs124 Tb, marketed by the company Invitrogen, having the formula below (which can be coupled to the compound to be labeled by a reactive group R), and the synthesis of which is described in U.S. Pat. No. 5,622,821.

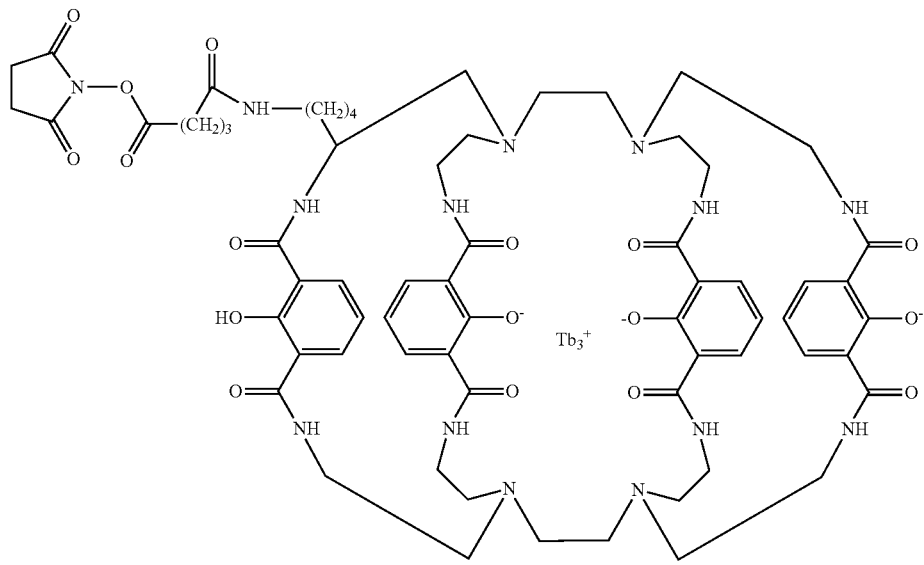

and the synthesis of which is described in international application WO 2008/063721.

The quantum dye from the company Research Organics, having the formula below (which can be coupled to the compound to be labeled by a reactive group, in this case NCS):

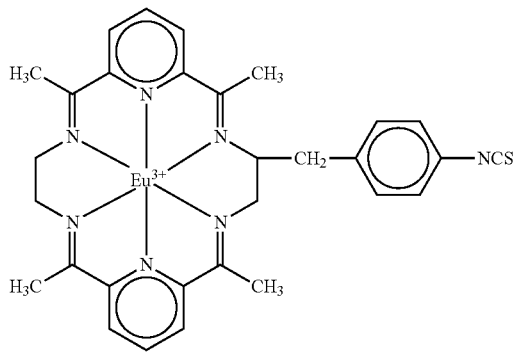

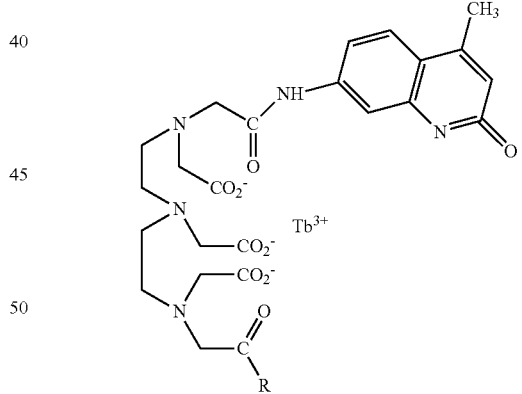

Complexes of dysprosium (Dy3+), of samarium (Sm3+), of neodymium (Nd3+), of ytterbium (Yb3+) or else of erbium (Er3+) are also rare earth complexes suitable for the purposes of the invention, complexes of europium (Eu3+) and of terbium (Tb3+) being particularly preferred.

A very large number of lanthanide complexes have been described, and several are currently exploited commercially in particular by the companies PerkinElmer, Invitrogen, Molecular Devices and Cisbio Bioassay. FIG. 1 shows other examples of europium and terbium complexes which can be used for the purposes of the invention.

Although the use of a fluorescent metal complex is one of the essential features of the invention, said invention is not limited to a given type of fluorescent metal complex, and those skilled in the art are able to select, from fluorescent metal complexes, those which are the most suitable for their particular use and which have a lifetime of greater than 0.1 ms, preferably between 0.5 and 6 ms.

According to the invention, the fluorescent metal complex is conjugated, i.e. covalently bonded, to a coupling agent which will allow direct or indirect labeling of the protein of interest by the fluorescent metal complex. These coupling agents are described in the section "labeling of proteins of interest" and are preferably a member of a ligand/receptor pair, for instance an anti-tag antibody, biotin, or else a substrate of a "suicide" enzyme, such as a derivative of benzylguanine, of benzylcytosine or of a chloroalkane.

The conjugation of a fluorescent metal complex with a coupling agent is part of the general knowledge of those skilled in the art and is based on the use of reaction groups. Commercially available rare earth complexes comprise a reaction group which allows this conjugation to a coupling agent, or already comprise such a coupling agent and are ready for use.

B. Modulating Compound

B.1: The Modulating Compound is an Energy Acceptor

In one of the embodiments of the method according to the invention, use is made of a modulating compound capable of modifying the signal emitted by the fluorescent metal complex through the phenomenon of Förster resonance energy transfer (FRET) from the fluorescent metal complex (the energy donor) to the modulating compound (the energy acceptor). This phenomenon, well known to those skilled in the art, is based on energy transfer between two FRET partner compounds, when they are in proximity to one another, in the present case between the fluorescent metal complex and the modulating compound which diffuses freely in the reaction medium.

In general, the use of the FRET phenomenon for studying biological processes implies that the members of the pair of FRET partners each be conjugated to compounds which will interact with one another, and thus bring the FRET partners into proximity with one another, which will generate a FRET signal. In the method according to the invention, the energy acceptor is not conjugated to any compound and diffuses freely in the reaction medium, whereas the fluorescent metal complex is directly or indirectly coupled to the membrane protein of interest: the energy transfer between the two FRET partners depends only on the diffusion of the acceptor compound in the reaction medium, according to the DEFET phenomenon.

The inventors have determined the conditions necessary for the establishment of a DEFET between a fluorescent metal complex coupled to a membrane protein and an acceptor diffusing in the extracellular medium, these conditions also making it possible to observe a variation in signal when the protein of interest is internalized.

According to this embodiment, the experimental conditions to be used in order to observe a DEFET dependent on the internalization of the protein of interest and the fluorescent metal complex are the following:
- the fluorescent metal complex and the modulating compound are FRET partners;
- the lifetime of the fluorescent metal complex should be greater than 0.1 ms, preferably between 0.5 and 6 ms;
- the concentration of the modulating compound in the extracellular medium should be between 0.1 µM and 1 mM. Preferably, the concentration of this compound is between 1 µM and 100 µM, which makes it possible to work in the rapid diffusion limit and to measure a DEFET signal independent of the concentration of fluorescent metal complex;
- the modulating compound preferably should not cross the cell membrane. Furthermore, its diffusion constant should be sufficiently high. In general, a modulating compound having a weight of less than 50 kD, preferably between 0.1 and 10 kD, is suitable for the purposes of the invention.

In this embodiment of the method according to the invention, the modulating compound may be fluorescent or nonfluorescent.

In the case where the modulating compound is a fluorescent energy-acceptor compound and the lanthanide is terbium or europium, this modulating compound may be selected from the following compounds or compound families: the cyanin derivatives, DY647, D2, fluorescein and its derivatives, coumarin, rhodamine, carbopyronine, oxazine and its analogs, Alexa Fluors, crystal violet, fluorophores of perylene bisimide type, squaraines, boron dipyrromethene derivatives, known under the trade name BODIPY®, NBD (nitrobenzoxadiazole) and its derivatives, DABCYL (4-((4-(dimethylamino)phenyl)azo)benzoic acid).

The Alexa Fluor compounds and the boron dipyrromethene derivatives are marketed by the company Invitrogen; the compound Dy647 is a cyanin derivative marketed by the company Dyomics; the cyanin derivatives are also marketed in particular by the company Amersham Biosciences; the other compounds are marketed by various suppliers of chemical reagents, such as the companies Sigma, Aldrich or Acros.

Nonfluorescent compounds can also be used, with the proviso that their absorption spectrum is compatible with the emission spectrum of the fluorescent metal complex. The following nonfluorescent acceptors are commercially available: the QXL products from the company Anaspec, and in particular QXL 570, QXL 610, QXL 670 and QXL 680; the DYQ660 and DYQ661 products from the company Dyomics and the QSY7, QSY9 and QSY21 products from the company Invitrogen.

The signal detected in the reaction medium may be: the luminescence emitted by the fluorescent metal complex, or, in the case where the acceptor compound is also fluorescent, the luminescence emitted by the acceptor compound, their intensity or their lifetime. In any event, these signals are dependent on the DEFET phenomenon and will vary during the internalization of the transmembrane protein of interest, in the following way:
- the intensity or the lifetime of the luminescence of the fluorescent metal complex measured at its emission wavelength will increase if the transmembrane protein is internalized;
- if the modulator is a fluorescent acceptor compound the intensity or the lifetime of the signal measured at the emission wavelength of the acceptor will change when the protein is internalized. It should be noted that the signal from the acceptor compound depends on the DEFET with the fluorescent metal complex, but also on possible intermolecular luminescence-quenching effects, occurring in the extracellular medium when the concentration of acceptor compound is high. For this reason, after internalization, the signal emitted at the emission wavelength of the acceptor modulating compound can increase or decrease;
- if the modulator is a fluorescent acceptor compound, its signal can be corrected by calculating the acceptor signal/donor signal ratio. This method of ratiometric correction of the FRET signal is widely used and described in the literature.

B2: The Modulating Compound is a Reducing Agent with Respect to the Fluorescent Metal Complex:

The inventors have discovered that reducing agents capable of decreasing the luminescence of the fluorescent metal complexes by means of oxidation-reduction reactions at the level of the fluorescent metal complex and/or of the complexing structure can be advantageously used in the method according to the invention.

The reducing agent should have a redox potential which is suitable for reducing the fluorescent metal complex. Those skilled in the art are capable, according to the fluorescent metal complex selected, of determining which reducing agents are suitable for carrying out the method according to the invention, but reducing agents of which the redox potential is between +0.1 and +1.2 V are preferred. Even more preferably, the redox potential of the reducing agent is between +0.25 and +0.75 V.

Thus, when the compound which modulates the signal emitted by the fluorescent metal complex is a reducing agent, it can be selected, for example, from the following reducing agents: iodides, ascorbates, urates, catecholates, inorganic compounds such as $Fe(CN)_6^{2+}$. These ions are added to the measuring medium in the form of salts with a counterion, for example for anions, in the form of sodium or potassium salts.

In this embodiment, the signal measured will correspond to the luminescence emitted by the fluorescent metal complex, modulated by the reducing agent present in the extracellular medium: when the protein of interest coupled to the fluorescent metal complex is internalized, the fluorescent metal complex is not in contact or in proximity with the modulating agent and its luminescence will be greater than in the case where internalization does not take place, as will its lifetime.

In this embodiment, and in order to be able to measure a difference in signal between the case where there is internalization and the case where internalization does not take place, the inventors have determined that the reducing agent should be present in the reaction medium at a concentration greater than or equal to the Stern-Volmer constant of the fluorescent metal complex/reducing agent pair. This constant is defined as being the concentration of reducing agent necessary to cause a 50% decrease in the intensity of fluorescent metal complex luminescence. Examples of Stern-Volmer constants for fluorescent metal complex/reducing agent pairs are given in particular in an article by Kielar et al. (Org. Biomol. Chem., 2007, 5, 2975-2982).

Thus, in a first aspect of this embodiment, it is the luminescence of the fluorescent metal complex which is measured.

In a second aspect of this embodiment, the first step of the method according to the invention comprises adding to the measuring medium a first fluorescent metal complex and a second fluorescent metal complex which are intended to label the protein of interest.

This second fluorescent metal complex is identical to the first complex, except for the metal, which is different. For example, the first fluorescent metal complex is a europium complex and the second metal complex is a terbium complex comprising the same chelating structure. In this embodiment, a given protein of interest is therefore potentially either directly or indirectly bound to the first fluorescent metal complex, or directly or indirectly bound to the second fluorescent metal complex (or is not labeled by any fluorescent metal complex).

In this embodiment, it is possible to standardize the signal measured, for example by forming a ratio of the luminescence emitted by one of the lanthanide complexes with the intensity of the luminescence emitted by the second fluorescent metal complex. This type of measurement makes it possible to compare the signals obtained from different reaction media, and is therefore particularly suitable for carrying out quantitative studies.

B3: The Modulating Compound is an Agent which Binds Specifically, by Noncovalent Bonding, with the Fluorescent Metal Complex:

The modulating compound may be an agent which has a domain allowing specific and noncovalent bonding with the fluorescent metal complex: these compounds can in fact cause a decrease in the luminescence of the fluorescent metal complex. These compounds can be selected from: antibodies or antibody fragments, peptides, or aptamers, each having a fluorescent-metal-complex-binding domain.

Among these agents, the preferred modulators are antibodies or antibody fragments capable of recognizing a fluorescent metal complex. Application WO2007/116069(A1) describes the preparation of antibodies specific for rare earth complexes, and those skilled in the art have, moreover, at their disposal techniques allowing them to produce compounds of this type.

In order to carry out the method according to the invention with this type of modulator, it is advisable to add the compound capable of causing the internalization before adding the modulating agent, which would otherwise be internalized at the same time as the fluorescent metal complex. In other words, in this embodiment, the steps of the method described above should be carried out in the following order: a), c), b), d), e).

B4: The Modulating Compound is a Metal Ion Which Competes with the Rare Earth so as to Form a Nonfluorescent Metal Complex:

Another type of modulator which is suitable for carrying out the method according to the invention is a metal ion which will compete with the rare earth so as to form a nonfluorescent complex with the complexing agent. In the case of rare earth chelates, the modulating agent may thus be the $Mn^{2+}$ ion.

In this case, the modulating agent is added to the extracellular medium in the form of a salt with an appropriate counterion, for example in the form of $MnCl_2$.

In order to carry out the method according to the invention with this type of modulator, it is advisable to add the compound capable of causing the internalization before adding the modulating agent. In other words, in this embodiment, the steps of the method described above should be carried out in the following order: a), c), b), d), e).

C. Proteins of Interest—Labeling with a Fluorescent Metal Complex

C.1. Expression

The invention can be carried out with any of the membrane proteins capable of being internalized, with the proviso that they can be directly or indirectly coupled, in is their extracellular part, with a fluorescent metal complex.

The invention is particularly useful for studying the internalization of G-protein coupled receptors (hereinafter "GPCRs"), and receptor tyrosine kinases (hereinafter: "RTK"), one of the mechanisms of regulation of which is internalization, as previously mentioned. It is nevertheless possible to carry out the invention with other membrane proteins for which it is desired to verify whether or not they are internalized.

The proteins of interest are expressed in the cell membranes naturally, or else are expressed using conventional molecular biology techniques, in particular expression vectors stably or transiently introduced into the cells. The reagents for stably or transiently introducing heterologous DNA into cells are commercially available and the DNA sequences encoding the proteins of interest, in particular those encoding GPCRs and RTKs, are available in databases such as Genbank. When the proteins of interest are stably expressed by the cells, cytotoxicity phenomena may be observed owing to the presence of too large a number of GPCRs; in those cases, it may be advantageous to use an inducible expression system in order to limit the expression of the GPCRs.

Thus, the method according to the invention may comprise a preliminary step of transfecting cells with an expression vector encoding the protein of interest. As described hereinafter, this vector may also contain the sequence encoding a suicide enzyme allowing covalent labeling of the protein of interest with the fluorescent metal complex.

In one particular embodiment, a second expression vector is cotransfected with the one encoding the protein of interest, this expression vector comprising the sequence encoding β-arrestin 1. Although this coexpression is not essential for the implementation of the invention, it can make it possible to increase the sensitivity of the method since β-arrestin 1 can nonspecifically amplify internalization phenomena.

C.2. Labeling with a Fluorescent Metal Complex

One particularly easy embodiment of the invention consists in conjugating the fluorescent metal complex to a compound (ligand) known to be capable of binding to a protein of interest: the modified ligand, by binding to the protein of interest, allows indirect labeling of this protein.

Many techniques have been described for modifying proteins, and those skilled in the art are able to use the existing tools for coupling a protein to a fluorescent metal complex. In particular, the conventional molecular biology techniques make it possible to add, delete or modify a given domain of a protein.

The only feature essential to the implementation of the invention is that the fluorescent metal complex is coupled to the protein in such a way as to be in the extracellular medium, so that the luminescence signal emitted by the reaction medium is actually dependent on the presence in the extracellular medium of a modulating compound.

If the protein of interest is a GPCR or an RTK, the fluorescent metal complex will therefore be conjugated to this protein via a modification of its N-terminal (extracellular) domain so as to allow it to be directly or indirectly labeled with the fluorescent metal complex according to one of the techniques described hereinafter. By way of nonlimiting illustration, mention may be made of the following techniques for coupling a transmembrane protein with a fluorescent metal complex:

Indirectly (Noncovalently) Coupling the Protein of Interest with a Fluorescent Metal Complex The fluorescent metal complex can be coupled with the protein of interest by means of a pair of binding partners, at least one of which is protein in nature. In this approach, the protein of interest is fused with the binding partner which is protein in nature, by means of conventional molecular biology techniques (construction of an expression vector comprising a nucleotide sequence encoding the protein of interest, fused with that encoding the protein binding partner, and introduction of the expression vector into the cell). The fluorescent metal complex is covalently conjugated to the other binding partner, which here is referred to as coupling agent, which will then be added to the extracellular medium. The recognition of the binding partners allows indirect labeling of the protein of interest with the fluorescent metal complex.

By way of nonlimiting example of binding partners particularly suitable for implementing the invention, mention will be made of:

The pair consisting of the cysteine-cysteine-X-X-cysteine-cysteine sequence (SEQ ID No. 1) in which X is any amino acid and of a biarsenic compound. These biarsenic compounds can be readily labeled with an organic molecule of the fluorescein or rhodamine type (see B. A. Griffin et al. (1998) Science. 1998, 281, 269-271 and S. A. Adams et al. (2002) J. Am. Chem. Soc. 2002, 124, 6063-6076 for details about the technology).

The BTX (bungarotoxin) peptide, composed of a peptide of 13 amino acids which is recognized by bungarotoxin (BTX), can be coupled to a fluorescent molecule (see C. M. McCann et al. (2005), Biotechnique (2005), 38, 945-952).

The streptavidin/biotin pair: the streptavidin binding sequence (SBP-Tag) is a sequence formed by 38 amino acids which has a high affinity for biotin that can be prelabeled with a fluorescent metal complex (see C. M. McCann et al. (2005), Biotechnique (2005), 38, 945-952).

The sequence of the *E. coli* dihydrofolate reductase enzyme (eDHFR) which binds, specifically and with high affinity, ligands, such as trimethoprim, to which the fluorescent metal complex can be grafted according to the technology known as "Ligand link Universal labeling technology" from the company Active Motif.

Tag/anti-tag pairs are binding partners frequently used for labeling proteins. The term "tag" denotes a small protein "label" consisting of an amino acid sequence, generally but not necessarily quite short (less than 15 amino acids), which is fused to the protein of interest or else is naturally present in this protein. The term "anti-tag" denotes an antibody which binds specifically to said tag. In this embodiment, the anti-tag antibody is covalently bonded to the fluorescent metal complex. When the antibody thus labeled is added to the extracellular medium, it binds to the tag conjugated to the protein of interest, and the tag/anti-tag interaction allows indirect labeling of this protein with the fluorescent metal complex.

By way of nonlimiting example of tag/anti-tag pairs, mention may be made of the following pairs, the members of which are commercially available: GST/anti-GST antibody in which GST represents glutathione S-transferase or a fragment thereof; 6HIS/anti-6HIS antibody in which 6HIS is a peptide consisting of 6 histidines; Myc/anti-Myc antibody in which Myc is a peptide consisting of amino acids 410-419 of the human Myc protein; FLAG/anti-FLAG antibody in which FLAG is a peptide having the 8 amino acids DYKDDDDK (SEQ ID No. 2); HA/anti-HA antibody in which HA is an influenza hemagglutinin epitope consisting of the 9 amino acids YPYDVPFYA (SEQ ID No. 3). It is clear that the exact nature of the tag is not essential for the implementation of the invention.

Direct (Covalent) Coupling of the Protein of Interest with a Fluorescent Metal Complex In this approach, the fluorescent metal complex will be coupled to the protein of interest by covalent bonding; several techniques have been described and the reagents necessary for implementing said techniques are commercially available. For this coupling, any one of the techniques hereinafter may be used:

Formation of a covalent bond at the level of a reactive group present on the protein of interest, in particular at the level of one of the following groups: the terminal amino group, the terminal carboxylate group, the carboxylate groups of aspartic acids and glutamic acids, the amine groups of lysines, the guanidine groups of arginines, the thiol groups of cysteines, the phenol groups of tyrosines, the indole rings of tryptophans, the thioether groups of methionines, the imidazole groups of histidines.

These groups present on the protein of interest can form a covalent bond with a reactive group borne by the fluorescent metal complex.

The suitable reactive groups are known to those skilled in the art: a fluorescent metal complex functionalized with a maleimide group will for example be capable of covalently bonding with the thiol groups borne by the cysteines of the protein. Likewise, a fluorescent metal complex bearing an N-hydroxysuccinimide ester will be capable of covalently bonding to an amine of the protein of interest.

Use of a Suicide Enzyme:

The term "suicide enzymes" is intended to mean proteins which have an enzymatic activity modified by specific mutations which gives them the ability to rapidly and covalently bond a substrate. These enzymes are termed "suicide" since each one can bond just one fluorescent molecule, the activity of the enzyme being blocked by the attachment of the substrate. These enzymes consequently constitute a tool of choice for specifically labeling proteins of interest with a ratio of one fluorescent molecule for one protein. In this approach, a suicide enzyme is fused with the membrane protein, preferably in its N-terminal part, by conventional molecular biology techniques, and the substrate of the enzyme, covalently bonded to a donor/acceptor, is introduced into the extracellular medium. The enzymatic reaction results in covalent bonding of the labeled substrate to the enzyme, and therefore labeling of the membrane protein with the donor or the acceptor.

By way of nonlimiting example, mention may be made of the following enzymes:

mutants of O6-alkylguanine DNA alkyltransferase (AGT). The enzymes SNAP-tag (Juillerat et al., Chemistry & biology, Vol. 10, 313-317 April 2003) and CLIP-tag (Gautier et al., Chemistry and Biology, 15, 128-136, February 2008) marketed by the company NEB are mutants of human AGT, the substrates of which are, respectively, O6-benzylguanine (hereinafter abbreviated to BG) and O2-benzylcytosine (hereinafter abbreviated to BC). The enzyme N-AGT (Gronemeyer et al., Protein engineering, design & selection, vol. 19, No. 7, pp 309-3016, 2006) is another mutant of this enzyme, the reactivity of which with O6-benzylguanine is better than that of the SNAP-tag enzyme;

the mutant of a dehalogenase (HaloTag marketed by Promega) which also generates an enzymatic reaction of the suicide type (see WO 04/072232 A2), some of the substrates of which are made of the chloroalkane family, in particular chloroalkanes comprising the unit —NH—CH$_2$CH$_2$—O—CH$_2$CH$_2$—O—(CH$_2$)$_6$—Cl. In this case, the fluorescent metal complex will be conjugated to this type of unit;

the ACP protein (Acyl Carrier Protein), onto which, in the presence of phosphopantetheine transferase, the 4'-phosphopantetheine residue of coenzyme A is transferred on a serine of ACP (N. George et al., Journal of the American Chemical society, 126, (2004) p 8896-8897). When this approach is used to label the protein of interest with the fluorescent metal complex, it is necessary to add phosphopantetheine transferase to the reaction medium. The company NEB markets an ACP fragment under the trade name "ACP-Tag" for protein labeling.

When this approach is used to label the protein of interest, the cells are transfected with an expression plasmid comprising the DNA encoding a fusion protein comprising the suicide enzyme and the protein of interest. This plasmid may also comprise, upstream of the DNA encoding these proteins, the DNA encoding a tag such as, for example, the FLAG epitope, the myc epitope, or the influenza hemagglutinin (HA) epitope.

In order to be sure that the fusion protein will be expressed in the cell membrane, it may be useful to include in the expression plasmid, upstream of the sequence encoding the protein of interest and the suicide enzyme, the sequence encoding a membrane targeting peptide, such as the T8 signal peptide or the signal peptide of the mGluR5 receptor, the use of which for this purpose is known to those skilled in the art. Finally, it may also be desirable to be sure that the sequence encoding the protein of interest does not comprise any native membrane targeting sequence which could be the subject of post-translational cleavage of the bond between the protein of interest and the suicide enzyme: if this is the case, it is preferable not to introduce this domain into the expression plasmid.

In order for the enzymatic reaction to take place with the substrate of the enzyme present in the extracellular medium (such as a BG-fluorescent metal complex conjugate), it is necessary for the suicide enzyme to be exposed to the extracellular medium: when the N-terminal part of the natural protein of interest is exposed to the extracellular medium, which is the case for GPCRs and RTKs, the fusion protein will be constructed such that the suicide enzyme is expressed in the N-terminal part of the fusion protein, but always downstream of the membrane targeting peptide if it is present.

Finally, when a suicide enzyme is used to label the protein of interest with the fluorescent metal complex, and the protein of interest is a GPCR or an RTK, the invention comprises a preliminary step of transfecting the cells with an expression vector comprising the DNA sequence encoding a fusion protein, the N-terminal part of which comprises a suicide enzyme and the C-terminal part of which comprises the protein of interest.

The introduction into the extracellular medium of the substrate of the enzyme conjugated to a fluorescent metal complex will result in labeling of the protein of interest with this fluorescent metal complex.

In this embodiment, the expression vectors encoding a fusion protein selected from the following fusion proteins can be used:

suicide enzyme—protein of interest, or tag—suicide enzyme—protein of interest, or membrane targeting peptide—tag—suicide enzyme—protein of interest.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein.

Figure 1:
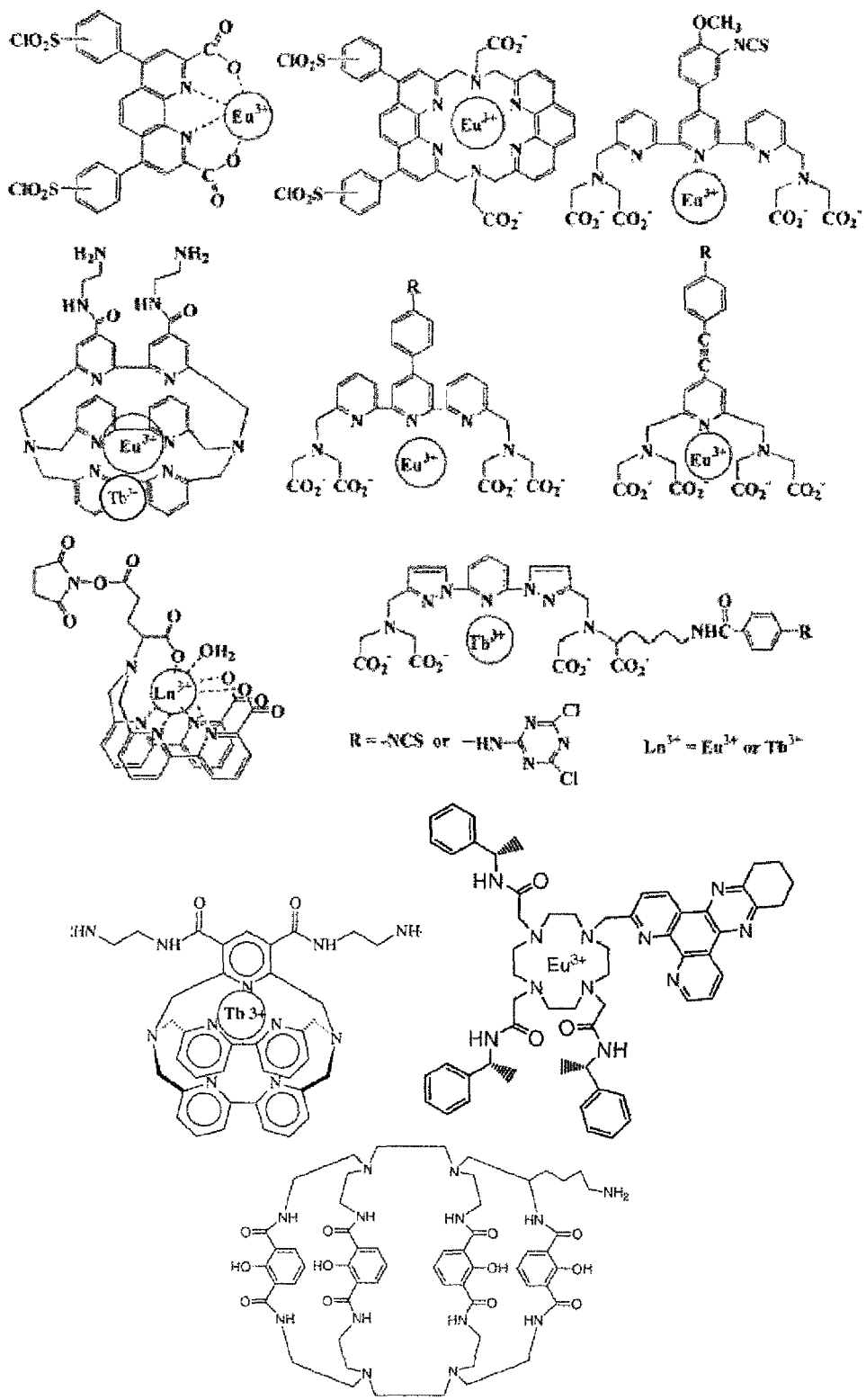
FIG. 1 shows representative examples of europium and terbium complexes which can be used for the purposes of the invention.

Without further elaboration, it is believed that one skilled in the art can, using the preceding description, utilize the following invention to its fullest extent. The following specific preferred embodiments are, therefore, to be construed as merely illustrative, and not limitative of the remainder of the disclosure in any way whatsoever.

EXAMPLES

The following examples illustrate preferred embodiments of the invention, namely those in which the fluorescent metal complex is a europium or terbium cryptate covalently bonded to benzylguanine or benzylcytosine, in which the protein of interest is expressed in the form of a fusion protein with an alkylguanine-DNA alkyltransferase mutant, and in which the modulating compound is a cyanin derivative, in particular Cy5 or Cy5-COOH, or fluorescein or one of its derivatives. When a europium cryptate is used, it is preferable to use the cyanin derivatives rather than fluorescein.

Example 1

Detection of Internalization of the Vasopressin Receptor V2-R

In this example, the intention is to detect the internalization of a fusion protein comprising the vasopressin V2 receptor, the Snap-tag enzyme and the HA tag, by means of the method according to the invention.

More specifically, a terbium cryptate (LUMI4-TB)—benzylguanine (BG) conjugate is in this case used as donor compound, the cyanin Cy5-COON is in this case used as acceptor, and the variations in signal resulting from a variation in DEFET subsequent to internalization of the receptor are observed.

Reagents and Materials Used
OptiMEM medium (Invitrogen (51985-026))
PBS phosphate buffer
DMEM woPR (DMEM culture medium without phenol red, Invitrogen)
DMEM+:DMEM to which the following have been added:
 1 mM L-alanyl/L-glutamine, 1 mM Na pyruvate, 10% fetal calf serum (Invitrogen SKU#10091-148), 1% penicillin-streptomycin (Invitrogen SKU#15070-063), 2 mM HEPES, 1% nonessential amino acids)
DMEM woPR+(DMEM+ medium without phenol red)
Krebs-Tris+glucose 0.5 g/l
BG-LUMI4-TB (benzylguanine-terbium cryptate conjugate, marketed by Cisbio Bioassay)
BG: $O^6$-benzylguanine (Sigma 82292)
Vasopressin (Bachem)
Plasmid HA-ST-V2: plasmid comprising the sequence encoding a fusion protein comprising a T8 membrane targeting signal peptide, the HA epitope, the SNAPTAG enzyme and the V2 receptor.
Cyanin Cy5-COOH: Eras Laboratories.

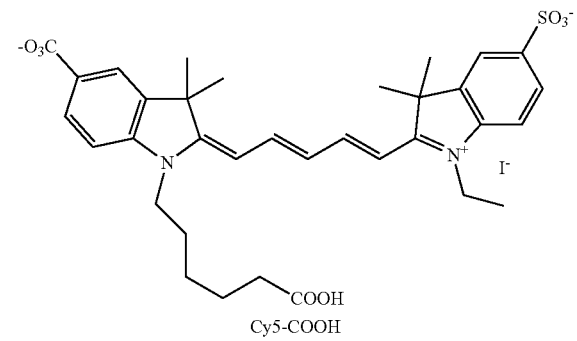

Cy5-COOH

Treatment of Plates

50 μl of solution of poly-L-ornithine (0.01% solution, molecular weight 30 000-70 000 (SIGMA P4957)) are distributed into each well of a 96-well plate (Cellstar, black with black bottom) in order to promote adhesion of the cells to the bottom of the well, and the plates are incubated for 30 minutes at 37° C., before being rinsed once with 100 μl of DMEM+.

Transfection

The following transfection mixture or a negative control mixture having the composition hereinafter are then distributed into the wells:

| Transfection mixture (per well): | Negative control mixture (per well): |
|---|---|
| 0.32 μg plasmid HA-ST-V2 (CIS BIO) | 0.32 μg plasmid PRK6 (CIS BIO) |
| 0.8 μl lipofectamine 2000 | 0.8 μl lipofectamine 2000 (Invitrogen) |
| 50 μl biological medium (DMEM+) | 50 μl biological medium (DMEM+) |

After incubation for 30 minutes, 100 μl of COS7 cells (CIS BIO), i.e. 80 000 cells, are added to each well, and then incubated for 24 hours at 37° C. in the presence of 5% $CO_2$.

Dose-Response Curve

The wells are rinsed once with DMEM woPR+ medium, before the addition of a solution of 156 nM of BG-LUMI4-TB or of 156 nM of BG (negative control) in DMEM woPR+ medium (100 μl), and the plate is then incubated for 1 hr 30 min.

Each well is then washed 3 times with 100 μl of Krebs-Tris buffer+glucose (0.5 g/l), before the addition of Krebs-Tris buffer, and then of vasopressin (V2 receptor agonist) diluted with the Krebs-Tris buffer (4° C., 10 μl, variable concentration, see plate plan).

After incubation for 30 minutes, 264 μM of Cyanin5-COOH in solution in the Krebs-Tris buffer (10 μl) are added to lines B, D, E-H (see plan) so as to obtain a final concentration of acceptor of 24 μM.

The plate is agitated for 15 minutes before being read on an Envision reader (PerkinElmer), fitted with a 337 nm nitrogen laser and with 545 nm and 665 nm emission filters. The reading is carried out in both channels with a delay of 400 μs and a reading window between 400 and 2900 μs.

The plan of the 96-well plate is represented below with the amounts of reagents added to each well:

| | 1-4 | 5-8 | 9-12 |
|---|---|---|---|
| A | PRK6<br>BG (110 μl, 156 nM) | PRK6<br>BG-LUMI4-TB (110 μl, 156 nM) | PRK6<br>BG-LUMI4-TB (100 μl, 156 nM)<br>Vasopressin (10 μl 10 μM) |
| B | PRK6<br>BG (100 μl, 156 nM)<br>Cy5 (10 μl, 264 μM) | PRK6<br>BG-LUMI4-TB (100 μl, 156 nM)<br>Cy5 (10 μl, 264 μM) | PRK6<br>BG-LUMI4-TB (90 μl, 156 nM)<br>Vasopressin (10 μl 10 μM)<br>Cy5 (10 μl, 264 μM) |
| C | HA-ST-$V_2$<br>BG (110 μl, 156 nM) | HA-ST-$V_2$<br>BG-LUMI4-TB (110 μl, 156 nM) | |
| D | HA-ST-$V_2$<br>BG (100 μl, 156 nM)<br>Cy5 (10 μl, 264 μM) | HA-ST-$V_2$<br>BG-LUMI4-TB (100 μl, 156 nM)<br>Cy5 (10 μl, 264 μM) | |
| E | HA-ST-$V_2$<br>BG (90 μl, 156 nM)<br>Cy5 (10 μl, 264 μM)<br>Vasopressin (10 μl, 10 pM) | HA-ST-$V_2$<br>BG (90 μl, 156 nM)<br>Cy5 (10 μl, 264 μM)<br>Vasopressin (10 μl, 100 pM) | |
| F | HA-ST-$V_2$<br>BG (90 μl, 156 nM)<br>Cy5 (10 μl, 264 μM)<br>Vasopressin (10 μl, 1 nM) | HA-ST-$V_2$<br>BG (90 μl, 156 nM)<br>Cy5 (10 μl, 264 μM)<br>Vasopressin (10 μl, 10 nM) | |
| G | HA-ST-$V_2$<br>BG (90 μl, 156 nM)<br>Cy5 (10 μl, 264 μM)<br>Vasopressin (10 μl, 100 nM) | HA-ST-$V_2$<br>BG (90 μl, 156 nM)<br>Cy5 (10 μl, 264 μM)<br>Vasopressin (10 μl, 1 μM) | |
| H | HA-ST-$V_2$<br>BG (90 μl, 156 nM)<br>Cy5 (10 μl, 264 μM)<br>Vasopressin (10 μl, 10 μM) | HA-ST-$V_2$<br>BG (90 μl, 156 nM)<br>Cy5 (10 μl, 264 μM)<br>Vasopressin (10 μl, 100 μM) | |

Line A: negative control with the plasmid PRK6, therefore no Snaptag (ST) labeling, signal observed in the absence of Cy5 acceptor, in the absence of LUMI4-TB donor (A1-A4), in the presence of LUMI4-TB donor without vasopressin (A5-A8) or with vasopressin (A9-A12).

Line B: negative control with plasmid PRK6, therefore no Snaptag (ST) labeling, signal observed in the presence of Cy5 acceptor, in the absence of LUMI4-TB donor (B1-B4), in the presence of LUMI4-TB donor without vasopressin (B5-B8) or with vasopressin (B9-B12). This line makes it possible to estimate the background noise in the absence of labeling of the receptor and makes it possible to correct the signals measured.

Line C: negative control with the plasmid HA-ST-$V_2$, therefore in the presence of Snaptag, but without vasopressin or Cy5 acceptor, signal observed in the presence of BG which is nonfluorescent (C1-C4) or fluorescent with the LUMI4-TB donor (C5-C12).

Line D: negative control with plasmid HA-ST-$V_2$, therefore in the presence of Snaptag, but without vasopressin, and in the presence of Cy5 acceptor; signal observed in the presence of BG which is nonfluorescent (D1-D4), or fluorescent with the LUMI4-TB donor (D5-D12). This line makes it possible to obtain the reference signal in the absence of internalization of the V2 receptor labeled with BG-LUM14-TB.

Lines E to H correspond to the signal observed in the presence of various concentrations of vasopressin.

Results & Discussion

Figure 2:
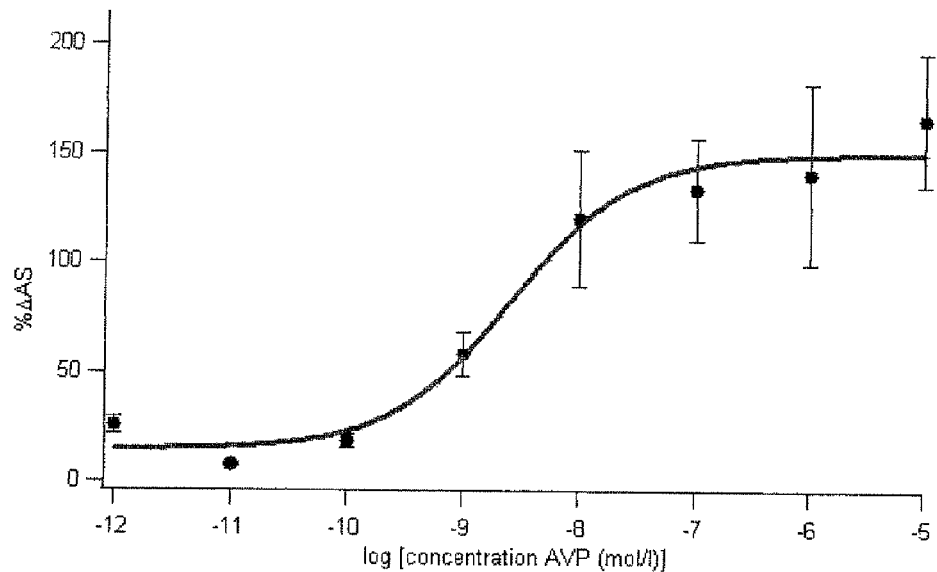
FIG. 2 shows the change in donor luminescence, measured at 545 nm, as a function of the vasopressin concentration and therefore as a function of the internalization of the receptor.

FIG. 2 represents the change in donor luminescence, measured at 545 nm, as a function of the vasopressin concentration and therefore as a function of the internalization of the receptor.

% ΔAS corresponds to the percentage increase in donor signal during internalization, relative to the reference signal measured without internalization (without vasopressin).

More specifically, for a given concentration of vasopressin, for example 10 pM (wells E1-E6), % ΔAS is calculated in the following way:

$$\% \Delta AS = \frac{([E1\text{-}E6]_{545} - [D5\text{-}D12]_{545})}{([D5\text{-}D12]_{545} - [D1\text{-}D4]_{545}) - ([B5\text{-}B8]_{545} - [B1\text{-}B4]_{545})}$$

In which "$[E1\text{-}E6]_{545}$", "$[D5\text{-}D12]_{545}$", etc., corresponds to the mean of the signals measured in the wells E1 to E6, D5 to D12, etc., at the wavelength of the BG-LUMI4-TB donor (545 nm).

The numerator corresponds to the difference between the signals measured in the presence and in the absence of vasopressin (and therefore of internalization) and the denominator corresponds to the reference signal in the absence of internalization ($[D5\text{-}D12]_{545}$) and corrected for the background noise ($[D1\text{-}D4]_{545}$, measured in the absence of BG-LUMI4-TB donor) and also for the nonspecific signal ($[B5\text{-}B8]_{545}$-$[B1\text{-}B4]_{545}$ in the absence of Snaptag labeling).

FIG. 2 shows a variation (in this case an increase) in the luminescence of the BG-LUMI4-TB donor compound at 545 in the presence of increasing concentrations of vasopressin, and therefore validates the use of the method according to the invention for demonstrating the internalization of membrane receptors.

Similar results are obtained if the focus is the signal emitted by the acceptor at 665 nm (Cy5), corrected for the donor signal at 545 (this ratiometric correction makes it possible to do away with the signal variability from one well to the other).

Figure 3:
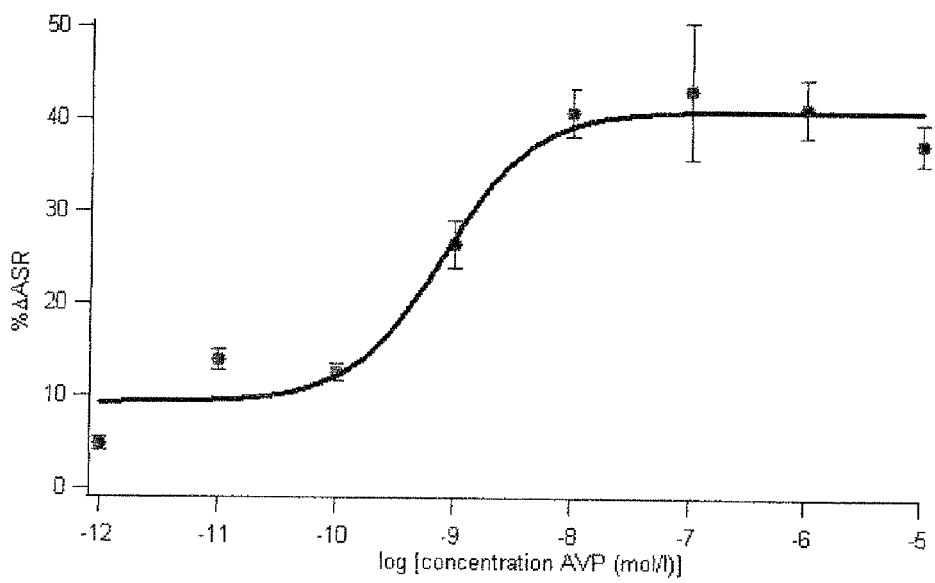
FIG. 3 shows the change of %MSR as a function of the vasopressin concentration and therefore of the internalization of the V2 receptor. % ΔASR corresponds to the percentage of the reference signal without internalization (measured in the absence of vasopressin).

FIG. 3 represents the change of % ΔASR as a function of the vasopressin concentration and therefore of the internalization of the V2 receptor. % ΔASR corresponds to the percentage of the reference signal without internalization (measured in the absence of vasopressin).

For a given concentration of vasopressin, for example 10 pM (wells E1-E6), % ΔASR is calculated in the following way:

$$\% \Delta ASR = 1 - \frac{[E1-E6]_{665} - [D1-D4]_{665} - ([B5-B8]_{665} - [B1-B4]_{665})}{[E1-E6]_{545} - [D1-D4]_{545} - ([B5-B8]_{545} - [B1-B4]_{545})} \cdot$$

$$\frac{[D5-D12]_{665} - [D1-D4]_{665} - ([B5-B8]_{665} - [B1-B4]_{665})}{[D5-D12]_{545} - [D1-D4]_{545} - ([B5-B8]_{545} - [B1-B4]_{545})}$$

The signal measured in the presence of vasopressin ($[E1-E6]_{665}/[E1-E6]_{545}$) and the reference signal ($[D1-D12]_{665}/[D1-D12]_{545}$) are each corrected for the background noise ([D1-D4], measured in the absence of BG-LUMI4-TB donor) and for the nonspecific signal ([B5-B8]-[B1-B4]) measured in the absence of Snaptag labeling.

FIG. 3 shows a variation (a decrease in the signal emitted by the acceptor compound) when increasing concentrations of vasopressin are present in the medium, and therefore validates the use of the method according to the invention for demonstrating the internalization of membrane receptors.

Example 2

Detection of Internalization of the Vasopressin Receptor V2-R

This example illustrates another embodiment of the method according to the invention for detecting internalization of the V2 vasopressin receptor. In particular, fluorescein was studied as acceptor and the expression plasmid encoding the V2 receptor was cotransfected with a plasmid encoding β-arrestin 1. This cotransfection made it possible to promote receptor internalization and therefore to increase the sensitivity of the method.

Reagents and Materials Used
OptiMEM medium (Invitrogen (51985-026))
Krebs-glucose: Krebs buffer+0.5 g/l glucose
BG-LUMI4-TB (benzylguanine-terbium cryptate conjugate, marketed by Cisbio Bioassay)
BG: $O^6$-benzylguanine (Sigma B2292)
Vasopressin (Bachem)
Plasmid FLAG-ST-V2: plasmid comprising the sequence encoding a fusion protein comprising a T8 membrane targeting signal peptide, the FLAG epitope, the SNAPTAG enzyme and the V2 receptor. The sequence of this plasmid is SEQ ID No. 4
Plasmid Flag-Arrestin β1: plasmid comprising the sequence encoding a fusion protein comprising the FLAG epitope and human β-arrestin 1. The sequence of this plasmid is SEQ ID No. 5
Fluorescein (Sigma).

Treatment of Plates
50 μl of solution of poly-L-ornithine (0.01% solution, molecular weight 30 000-70 000 (SIGMA P4957)) were distributed into each well of a 96-well plate (Cellstar, black with black bottom) in order to promote adhesion of the cells to the bottom of the well, and the plates were incubated for 30 min at 37° C.

Transfection
The following transfection mixture was then distributed into each well:
0.16 μg of plasmid FLAG-ST-V2+0.16 μg of plasmid Flag-β1 Arrestin
0.8 μl lipofectamine 2000
50 μl of OptiMEM medium.

After incubation for 30 minutes, 100 μl of a suspension containing 100 000 COS7 cells were added to each well, and then incubated for 24 hours at 37° C. in the presence of 5% of $CO_2$.

Dose-Response Curve
The transfection medium was drawn off and a solution of 100 nM of BG-LUMI4-TB in Krebs-glucose medium was added to each well. The plate was then incubated for 1 hr at 37° C. in the presence of $CO_2$.

Each well was then washed 4 times with 100 μl of Krebs-glucose before the addition of 90 μl of Krebs-glucose buffer or of a solution of vasopressin.

After incubation for 30 minutes at +37° C. and 5% $CO_2$, 10 μl of fluorescein in solution at 240 μM in Krebs-glucose buffer were added to the wells so as to obtain a final concentration of acceptor of 24 μM.

The plate was subsequently gently agitated and then read on a Rubystar reader (BMG) fitted with a 337-nm nitrogen laser and with 620 nm and 520 nm emission filters. The reading was carried out for the acceptor channel (520 nm) with a delay of 60 μs and a reading window of 60 to 400 μs, and for the donor channel (620 nm) with a delay of 400 μs for a window of 400 to 1500 μs.

Figure 4:
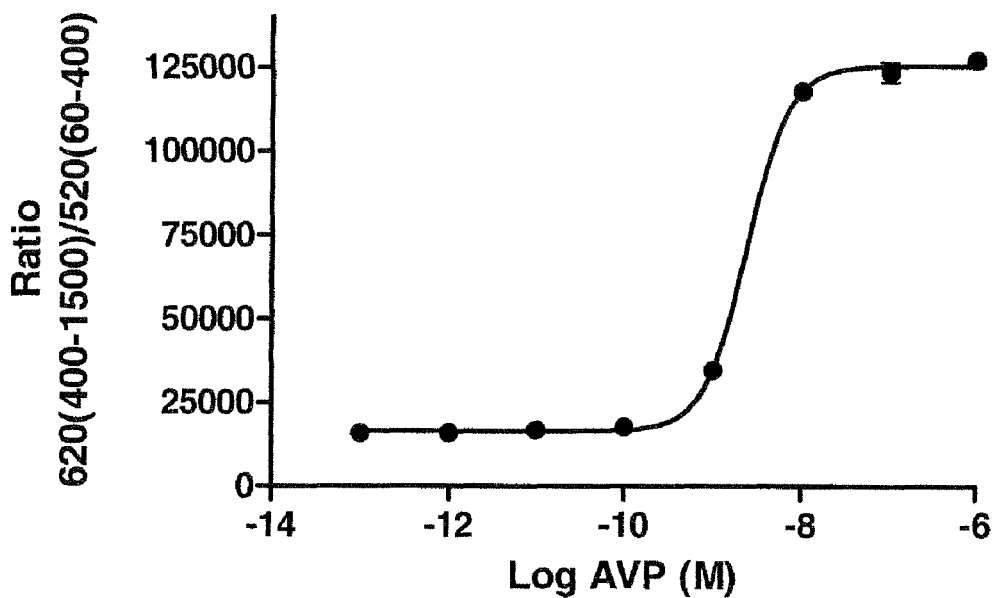
FIG. 4 shows the change in the ratio of the donor signal (measured at 620 nm) to the acceptor signal (measured at 520 nm), as a function of the vasopressin concentration (AVP). This ratio makes it possible to be free of inter-well variations. Moreover, it was multiplied by 10 000 in order to facilitate the graphic representation thereof.

Results & Discussion
FIG. 4 represents the change in the ratio of the donor signal (measured at 620 nm) to the acceptor signal (measured at 520 nm), as a function of the vasopressin concentration (AVP). This ratio makes it possible to be free of inter-well variations. Moreover, it was multiplied by 10 000 in order to facilitate the graphic representation thereof.

FIG. 4 shows very clearly that an increasing concentration of vasopressin causes an increase the ratio, corresponding to an increase in the luminescence of the donor compound.

The addition of vasopressin in fact causes internalization of the V2 receptors to which the BG-LUMI4-Tb donor conjugates are bound, and consequently an increase in their luminescence since they are no longer involved in DEFET phenomena with the fluorescein in solution in the extracellular medium.

This example therefore shows once again the excellent correlation between the increase in the signal of the donor compound corresponding to a decrease in DEFET and the internalization of the V2 receptor in the presence of its agonist, vasopressin. This example also shows how the method according to the invention can be used to demonstrate compounds which are agonists of a receptor of interest.

Example 3

Effect of the V2 Receptor Antagonist EDA9 on Vasopressin-Induced Internalization of the V2 Receptor This example illustrates the use of the method according to the invention to demonstrate a compound which is a vasopressin V2 receptor antagonist. A compound which is a known antagonist of this receptor, EDA9 (PolyPeptide-group) is used for this.

The reagents and materials used are the same as those of example 2. The same is true of the treatment of the plates and the reagents and protocols for transfection.

Dose-Response Curve in the Presence of EDA9 Antagonist

The transfection medium was drawn off and a solution of 100 nM of BG-LUMI4-TB in Krebs-glucose medium was added to each well. The plate was then incubated for 1 hr at 37° C. in the presence of $CO_2$.

Each well was then washed 4 times with 100 μl of Krebs-glucose before the addition of 45 μl of Krebs-glucose buffer or of a solution of EDA9.

After incubation for 30 minutes at +37° C. and 5% $CO_2$, 45 μl of a solution of vasopressin at 160 nM were added to the wells so as to obtain a final concentration of vasopressin of 80 nM in each well.

After incubation for 30 minutes at +37° C. and 5% $CO_2$, 10 μl of fluorescein in solution at 240 μM in Krebs-glucose buffer were added to the wells so as to obtain a final concentration of acceptor of 24 μM.

The plate was then gently agitated and then read on an Envision reader (Perkin Elmer) fitted with a 337-nm nitrogen laser and with 620-nm and 520-nm emission filters. The reading was carried out for the acceptor channel (520 nm) with a delay of 60 μs and a reading window of 60 to 400 μs, and for the donor channel (620 nm) with a delay of 400 μs for a window of 400 to 1500 μs.

Results & Discussion

Figure 5:
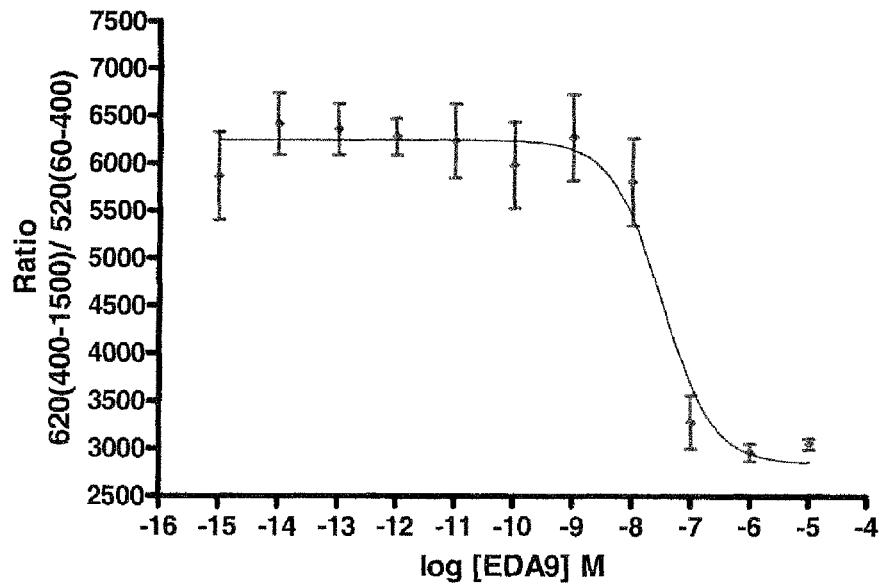
FIG. 5 shows the change in the ratio of the donor signal (measured at 620 nm) to the acceptor signal (measured at 520 nm), as a function of the concentration of EDA9 antagonist and in the presence of a constant concentration of vasopressin (AVP). The ratio calculated is multiplied by 10 000 in order to facilitate the graphic representation thereof.

FIG. 5 represents the change in the ratio of the donor signal (measured at 620 nm) to the acceptor signal (measured at 520 nm), as a function of the concentration of EDA9 antagonist and in the presence of a constant concentration of vasopressin (AVP). The ratio calculated is multiplied by 10 000 in order to facilitate the graphic representation thereof.

FIG. 5 shows a decrease in the ratio when the concentration of EDA9 antagonist increases. This decrease can be explained by a decrease in the donor signal: in the absence of EDA9 and in the presence of vasopressin, the V2 receptors are internalized, and the donor is not involved in DEFET with the acceptor present in the extracellular medium. In the presence of EDA9 antagonist which competes with the vasopressin for binding to the receptor, the V2 receptors are less activated, and therefore less internalized, and the donor is therefore involved in DEFET with the acceptor in solution and its luminescence is consequently lower than in the absence of EDA9.

This example therefore shows that the method according to the invention, by making it possible to detect the internalization of a receptor, can make it possible to demonstrate not only agonist compounds for this receptor, but also antagonist compounds.

Example 4

Detection of Internalization of the CXCR7 Chemokine Receptor

This example concerns the detection of internalization of the CXCR7 receptor caused by the action of one of its agonists, SDF-1 (acronym of the name of this molecule, "Stromal Cell-derived factor 1"). The protocol for carrying out this example is similar to that of example 2.

The reagents and procedures that were used are the same as those of example 2, with the exception of the plasmid FLAG-ST-V2 which was replaced with the plasmid FLAG-ST-CXCR7 (SEQ ID No. 6), and of the vasopressin which is replaced with SDF-1 (Laboratoire Pasteur, Paris).

Results & Discussion

Figure 6:
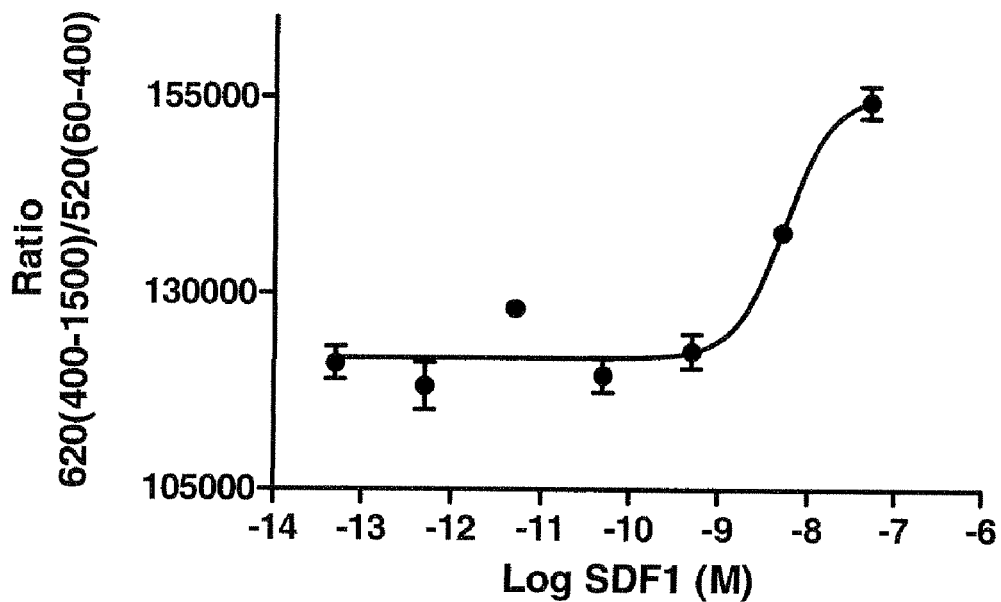
FIG. 6 shows the change in the ratio of the donor signal (measured at 620 nm) to the acceptor signal (measured at 520 nm), as a function of the concentration of SDF-1. This ratio makes it possible to be free of inter-well variations. Moreover, it was multiplied by 10 000 in order to facilitate the graphic representation thereof.

FIG. 6 represents the change in the ratio of the donor signal (measured at 620 nm) to the acceptor signal (measured at 520 nm), as a function of the concentration of SDF-1. This ratio makes it possible to be free of inter-well variations. Moreover, it was multiplied by 10 000 in order to facilitate the graphic representation thereof.

FIG. 6 shows very clearly that an increasing concentration of SDF-1 causes an increase in the ratio, reflecting an increase in the luminescence of the donor compound.

This example therefore shows the excellent correlation between the increase in the signal of the donor compound corresponding to a decrease in DEFET and internalization of the CXCR7 receptor in the presence of SDF-1 agonist. This example also supports the fact that the method according to the invention can be generalized to all receptors of which the activation leads to internalization.

Example 5

Detection of Internalization of the β2-Adrenergic Receptor

This example is similar to example 2, but focuses on the detection of internalization of the β2-adrenergic receptor caused by the action of one of its agonists, isoproterenol.

The reagents and procedures that were used are the same as those of example 2, with the exception of the plasmid FLAG-ST-V2 which was replaced with the plasmid FLAG-ST-β2AR (SEQ ID No. 7), and of the vasopressin which is replaced with isoproterenol (Tocris).

Results & Discussion

Figure 7:
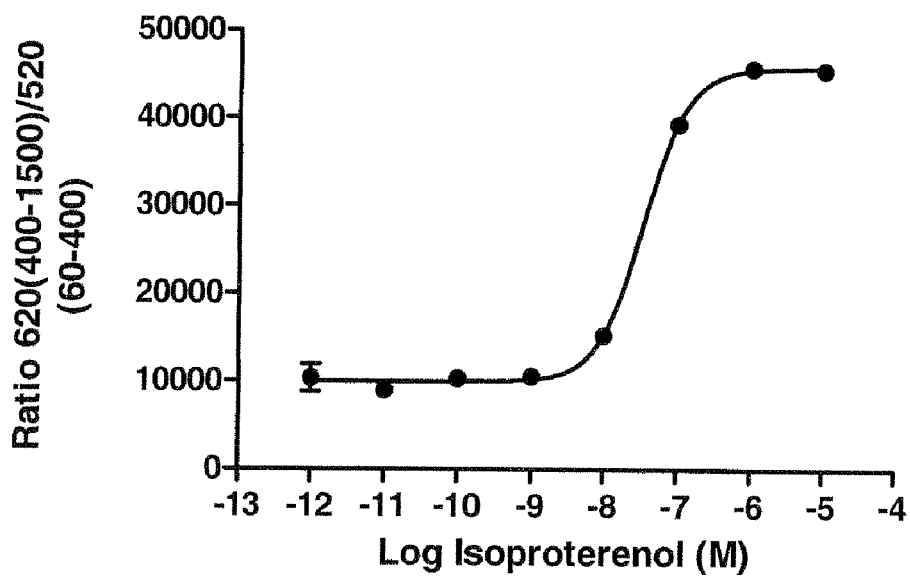
FIG. 7 shows the change in the ratio of the donor signal (measured at 620 nm) to the acceptor signal (measured at 520 nm), as a function of the concentration of isoproterenol. This ratio makes it possible to be free of inter-well variations. Moreover, it was multiplied by 10 000 in order to facilitate the graphic representation thereof.

FIG. 7 represents the change in the ratio of the donor signal (measured at 620 nm) to the acceptor signal (measured at 520 nm), as a function of the concentration of isoproterenol. This ratio makes it possible to be free of inter-well variations. Moreover, it was multiplied by 10 000 in order to facilitate the graphic representation thereof.

FIG. 7 shows very clearly that an increasing concentration of isoproterenol causes an increase in the ratio, reflecting an increase in the luminescence of the donor compound.

This example therefore shows the excellent correlation between the increase in the signal of the donor compound corresponding to a decrease in DEFET and internalization of the β2-adrenergic receptor in the presence of isoproterenol. This example also supports the fact that the method according to the invention can be generalized to all receptors of which the activation leads to internalization.

The invention claimed is:

1. A method for detecting the internalization of a transmembrane protein of interest expressed at the surface of a cell which is contained in a reaction medium, comprising:
   a) labeling, in said reaction medium, the protein of interest with a fluorescent metal complex comprising a lanthanide or ruthenium, the lifetime of which is greater than 0.1 ms;
   b) adding to said reaction medium a compound capable of causing the internalization of the protein of interest;
   c) adding to said reaction medium a modulating agent which is a fluorescent FRET acceptor compound compatible with said fluorescent metal complex, wherein said the acceptor is not conjugated to a compound which can bring said acceptor into proximity with said fluorescent metal complex, and wherein the acceptor freely diffuses in the reaction medium, the final concentration of which in the reaction medium is greater than $10^{-7}$ M, and the molecular weight of which is less than 50 kD;
   d) measuring the signal emitted by said reaction medium at the emission wavelength of the fluorescent metal complex and/or at the emission wavelength of the modulating agent when said modulating agent is a fluorescent acceptor compound;
   e) comparing the signal measured in step d) with a reference signal measured on cells having been subjected only to steps a), c) and d), a difference in the signal measured in step d) compared with the reference signal being representative of the internalization of the protein of interest.

2. The method of claim 1, wherein the steps are carried out in the following order: a), b), c), d), e).

3. The method of claim 2, which further comprises a washing step between step a) and step b).

4. The method of claim 1, wherein the steps are carried out in the following order: a), c), b), d), e).

5. The method of claim 4, which further comprises a washing step between step a) and step c).

6. The method of claim 1, wherein the lifetime of the fluorescent metal complex is between 0.5 and 6 ms.

7. The method of claim 1, wherein the fluorescent metal complex is:
   a) a lanthanide complex in which the lanthanide is selected from the group consisting of europium, terbium, neodymium, samarium and dysprosium; or
   b) a ruthenium complex.

8. The method of claim 7, wherein the fluorescent metal complex is a lanthanide chelate or cryptate.

9. The method of claim 8, wherein the fluorescent metal complex comprises (i) between 2 and 9 electron-donor heteroatoms selected from N, O and S, these atoms forming coordination bonds with the lanthanide or the ruthenium, and (ii) one or more chromophores comprising aromatic structures, comprising 1, 2 or 3 heteroatoms selected from N and O, which play the role of lanthanide or ruthenium coordination atoms.

10. The method of claim 1, wherein the modulating agent is a fluorescent FRET acceptor compound compatible with the fluorescent metal complex, the final concentration of which in the reaction medium is greater than $10^{-7}$ M and the molecular weight of which is less than 50 kD.

11. The method of claim 10, wherein the final concentration of the FRET acceptor compound in the reaction medium is between $10^{-6}$ M and $10^{-3}$ M, and wherein its molecular weight is between 0.1 and 10 kD.

12. The method of claim 1, wherein the modulating agent is a fluorescent acceptor compound selected from the group consisting of: cyanin derivatives, fluorescein, coumarin, rhodamine, carbopyronine, oxazine and its analogs, Alexa Fluor fluorophores, Crystal violet, perylene bisimide fluorophores, squaraine fluorophores, boron dipyrromethene derivatives, NBD (nitrobenzoxadiazole) and its derivatives, and DABCYL (4-((4-(dimethylamino)phenyl)azo)benzoic acid).

13. The method of claim 1, wherein the modulating agent is a fluorescent acceptor compound selected from the group consisting of: fluorescein and its derivatives, and cyanin derivatives.

14. The method of claim 1,
wherein the modulating agent is a nonfluorescent acceptor compound selected from the group consisting of QXL 570, QXL 610, QXL 670 and QXL 680; DYQ660 and DYQ661; QSY7, QSY9 and QSY21.

15. The method of claim 1, wherein the modulating compound is a reducing agent selected from the group consisting of iodide, ascorbate, urate, catecholate, and $Fe(CN)_6^{2+}$.

16. The method of claim 15, wherein the modulating agent is a reducing agent and step a) comprises adding a first fluorescent metal complex and adding a second fluorescent metal complex, said fluorescent metal complexes having the same chelating structures but being complexed with different metals.

17. The method of claim 16, wherein the first metal complex is a europium complex and the second metal complex is a terbium complex, the terbium and europium complexes having the same chelating structure.

18. The method of claim 1, wherein the modulating compound is an agent which binds specifically, by noncovalent bonding, to the fluorescent metal complex, selected from the group consisting of antibodies, antibody fragments, peptides and aptamers, each having a fluorescent-metal-complex-binding domain.

19. The method of claim 1, wherein the modulating compound is a metal ion which competes with the lanthanide or the ruthenium, so as to form a nonfluorescent metal complex.

20. The method of claim 19, wherein said ion is the manganese ion.

21. The method of claim 1, wherein the labeling of the protein of interest with the fluorescent metal complex is indirect labeling via a pair of binding partners, one of the members of which is covalently conjugated to the fluorescent metal complex, and the other member of which is covalently conjugated to the protein of interest or is naturally present on the protein of interest.

22. The method of claim 21, wherein the pair of binding partners is selected from the group consisting of the sequence CCXXCC (SEQ ID No. 1) wherein C=Cysteine and X=any amino acid/biarsenic compound;
a BTX peptide/bungarotoxin;
streptavidin or avidin/biotin;
an eDHFR fragment/trimethoprim; tag/anti-tag antibody;
a known ligand of the protein of interest/a protein of interest.

23. The method of claim 22, wherein the fluorescent metal complex is covalently bonded to an anti-tag antibody selected from the group consisting of
an antibody specific for the protein of interest; and
an antibody specific for a tag selected from the group consisting of GST, 6HIS, Myc, FLAG and HA, wherein the protein of interest contains the tag.

24. The method of claim 1, wherein the labeling of the protein of interest with the fluorescent metal complex is direct labeling by covalent bonding.

25. The method of claim 24, wherein the fluorescent metal complex is conjugated to a substrate of a suicide enzyme, and wherein the protein of interest is expressed in the form of a fusion protein, the extracellular part of which contains the suicide enzyme.

26. The method of claim 25, wherein the suicide enzyme/suicide enzyme substrate pair is selected from the group consisting of:
a pair alkylguanine-DNA alkyltransferase mutant/benzylguanine;
a pair alkylguanine-DNA alkyltransferase mutant/benzylcytosine;
a pair dehalogenase mutant/chloroalkane; and
a pair acyl carrier protein/coenzyme A in the presence of phosphopantetheine transferase.

27. The method of claim 24, wherein the fluorescent metal complex comprises a first reactive group capable of forming a covalent bond with a second reactive group present on the protein of interest.

28. The method of claim 27, wherein the fluorescent metal complex comprises a maleimide group intended to react with the thiol groups of the protein of interest.

29. The method of claim 1, wherein the fluorescent metal complex is a europium cryptate or a terbium cryptate covalently bonded to benzylguanine or benzylcytosine or one of their derivatives, and wherein the protein of interest is expressed in the form of a fusion protein with an alkylguanine-DNA alkyltransferase mutant.

30. The method of claim 1, wherein the fluorescent metal complex is a europium cryptate or a terbium cryptate covalently bonded to benzylguanine or benzylcytosine, wherein the protein of interest is expressed in the form of a fusion protein with an alkylguanine-DNA alkyltransferase mutant, and wherein the modulating agent is a cyanin derivative.

31. The method of claim 30, wherein the modulating agent is Cy5 or Cy5-COOH.

32. The method of claim 1, wherein the fluorescent metal complex is a terbium cryptate covalently bonded to benzylguanine or benzylcytosine, wherein the protein of interest is expressed in the form of a fusion protein with an alkylguanine-DNA alkyltransferase mutant, and wherein the modulating agent is fluorescein or one of its derivatives.

33. The method of claim 1, wherein the protein of interest is selected from the group consisting of: G-protein coupled receptors and receptor tyrosine kinases.

34. The method of claim 1, which further comprises a preliminary step of transfecting cells with an expression vector comprising the DNA sequence encoding the protein of interest.

35. The method of claim 34, wherein the expression vector comprises a sequence encoding a fusion protein, the N-terminal part of which comprises a suicide enzyme and the C-terminal part of which comprises the protein of interest, and wherein the protein of interest is a G-protein coupled receptor or a receptor tyrosine kinase.

36. The method of claim 34, wherein said transfection step additionally comprises cotransfecting a vector comprising the DNA sequence encoding β-arrestin 1.

* * * * *

SEQUENCE LISTING

<160> NUMBER OF SEQ ID NOS: 7

<210> SEQ ID NO 1
<211> LENGTH: 6

-continued

```
<212> TYPE: PRT
<213> ORGANISM: artificial sequence
<220> FEATURE:
<223> OTHER INFORMATION: binding partner
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

Cys Cys Xaa Xaa Cys Cys
1               5

<210> SEQ ID NO 2
<211> LENGTH: 8
<212> TYPE: PRT
<213> ORGANISM: artificial sequence
<220> FEATURE:
<223> OTHER INFORMATION: flag

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: artificial sequence
<220> FEATURE:
<223> OTHER INFORMATION: HA: influenza hemagglutinin epitope

<400> SEQUENCE: 3

Tyr Pro Tyr Asp Val Pro Phe Tyr Ala
1               5

<210> SEQ ID NO 4
<211> LENGTH: 7154
<212> TYPE: DNA
<213> ORGANISM: artificial sequence
<220> FEATURE:
<223> OTHER INFORMATION: plasmid FLAG-ST-V2
<220> FEATURE:
<221> NAME/KEY: promoter
<222> LOCATION: (232)..(819)
<223> OTHER INFORMATION: CMV_promoter
<220> FEATURE:
<221> NAME/KEY: sig_peptide
<222> LOCATION: (923)..(986)
<223> OTHER INFORMATION: signal peptide T8
<220> FEATURE:
<221> NAME/KEY: sig_peptide
<222> LOCATION: (923)..(986)
<223> OTHER INFORMATION: T8 signal peptide
<220> FEATURE:
<221> NAME/KEY: gene
<222> LOCATION: (1004)..(1027)
<223> OTHER INFORMATION: gene encoding the FLAG epitope_CDS
<220> FEATURE:
<221> NAME/KEY: gene
<222> LOCATION: (1046)..(1591)
<223> OTHER INFORMATION: gene encoding the Snap Tag enzyme_CDS
<220> FEATURE:
<221> NAME/KEY: gene
<222> LOCATION: (1598)..(2710)
<223> OTHER INFORMATION: gene encoding the V2 receptor_CDS
<220> FEATURE:
<221> NAME/KEY: polyA_signal
<222> LOCATION: (2754)..(2978)
<223> OTHER INFORMATION: BGH polyA_signal
<220> FEATURE:
<221> NAME/KEY: gene
<222> LOCATION: (3862)..(4656)
<223> OTHER INFORMATION: Neomycin resistance gene_CDS
```

<220> FEATURE:
<221> NAME/KEY: gene
<222> LOCATION: (6158)..(7018)
<223> OTHER INFORMATION: Ampicillin resistance gene_CDS

<400> SEQUENCE: 4

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagctttgag | acatggcctt | accagtgacc | gccttgctcc | tgccgctggc | 960 |
| cttgctgctc | cacgccgcca | ggccggccgc | cgctagcggc | atcgactaca | aggacgacga | 1020 |
| tgacaaggcc | ggcatcgatg | ccatcatgga | caaagactgc | gaaatgaagc | gcaccaccct | 1080 |
| ggatagccct | ctgggcaagc | tggaactgtc | tgggtgcgaa | cagggcctgc | acgagatcaa | 1140 |
| gctgctgggc | aaaggaacat | ctgccgccga | cgccgtggaa | gtgcctgccc | cagccgccgt | 1200 |
| gctgggcgga | ccagagccac | tgatgcaggc | caccgcctgg | ctcaacgcct | actttcacca | 1260 |
| gcctgaggcc | atcgaggagt | tccctgtgcc | agccctgcac | cacccagtgt | tccagcagga | 1320 |
| gagctttacc | cgccaggtgc | tgtggaaact | gctgaaagtg | gtgaagttcg | agagggtcat | 1380 |
| cagctaccag | cagctggccg | ccctggccgg | caatcccgcc | gccaccgccg | ccgtgaaaac | 1440 |
| cgccctgagc | ggaaatcccg | tgcccattct | gatccctgc | caccgggtgg | tgtctagctc | 1500 |
| tggcgccgtg | gggggctacg | agggcgggct | cgccgtgaaa | gagtggctgc | tggcccacga | 1560 |
| gggccacaga | ctgggcaagc | ctgggctggg | tgatatcctc | atggcgtcca | ccacttccgc | 1620 |
| tgtgcctggc | catccctctc | tgcccagcct | gccagcaac | agcagccagg | agaggccact | 1680 |
| ggacacccgg | gacccgctgc | tagcccgggc | ggagctggcg | ctgctctcca | tagtctttgt | 1740 |
| ggctgtggcc | ctgagcaatg | gcctggtgct | ggcggccta | gctcggcggg | gccggcgggg | 1800 |
| ccactgggca | cccatacacg | tcttcattgg | ccacttgtgc | ctggccgacc | tggccgtggc | 1860 |
| tctgttccaa | gtgctgcccc | agctggcctg | gaaggccacc | gaccgcttcc | gtgggccaga | 1920 |
| tgccctgtgt | cgggccgtga | agtatctgca | gatggtgggc | atgtatgcct | cctcctacat | 1980 |
| gatcctggcc | atgacgctgg | accgccaccg | tgccatctgc | cgtcccatgc | tggcgtaccg | 2040 |
| ccatggaagt | ggggctcact | ggaaccggcc | ggtgctagtg | gcttgggcct | ctcgctcct | 2100 |
| tctcagcctg | ccccagctct | tcatcttcgc | ccagcgcaac | gtggaaggtg | gcagcggggt | 2160 |

```
cactgactgc tgggcctgct tgcggagcc ctggggccgt cgcacctatg tcacctggat    2220
tgccctgatg gtgttcgtgg cacctaccct gggtatcgcc gcctgccagg tgctcatctt    2280
ccgggagatt catgccagtc tggtgccagg gccatcagag aggcctgggg ggcgccgcag    2340
gggacgccgg acaggcagcc ccggtgaggg agcccacgtg tcagcagctg tggccaagac    2400
tgtgaggatg acgctagtga ttgtggtcgt ctatgtgctg tgctgggcac ccttcttcct    2460
ggtgcagctg tgggccgcgt gggacccgga ggcacctctg gaaggggcgc cctttgtgct    2520
actcatgttg ctggccagcc tcaacagctg caccaacccc tggatctatg catctttcag    2580
cagcagcgtg tcctcagagc tgcgaagctt gctctgctgt gcccggggac gcaccccacc    2640
cagcctgggt ccccaagatg agtcctgcac caccgccagc tcctccctgg ccaaggacac    2700
ttcatcgtga ctcgagtcta gagggcccgt ttaaacccgc tgatcagcct cgactgtgcc    2760
ttctagttgc cagccatctg ttgtttgccc ctcccccgtg ccttccttga ccctggaagg    2820
tgccactccc actgtccttt cctaataaaa tgaggaaatt gcatcgcatt gtctgagtag    2880
gtgtcattct attctggggg gtggggtggg gcaggacagc aagggggagg attgggaaga    2940
caatagcagg catgctgggg atgcggtggg ctctatggct tctgaggcgg aaagaaccag    3000
ctggggctct aggggggtatc cccacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg ggccatcgcc ctgatagacg ttttcgcc ctttgacgtt    3300 ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttaattctgt ggaatgtgtg tcagttaggg    3480
tgtggaaagt ccccaggctc cccagcaggc agaagtatgc aaagcatgca tctcaattag    3540
tcagcaacca ggtgtggaaa gtccccaggc tccccagcag gcagaagtat gcaaagcatg    3600
catctcaatt agtcagcaac catagtcccg cccctaactc cgcccatccc gcccctaact    3660
ccgcccagtt ccgcccattc tccgccccat ggctgactaa ttttttttat ttatgcagag    3720
gccgaggccg cctctgcctc tgagctattc cagaagtagt gaggaggctt ttttggaggc    3780
ctaggctttt gcaaaaagct cccgggagct tgtatatcca ttttcggatc tgatcaagag    3840
acaggatgag gatcgtttcg catgattgaa caagatggat tgcacgcagg ttctccggcc    3900
gcttgggtgg agaggctatt cggctatgac tgggcacaac agacaatcgg ctgctctgat    3960
gccgccgtgt tccggctgtc agcgcagggg cgcccggttc ttttttgtcaa gaccgacctg    4020 tccggtgccc tgaatgaact gcaggacgag gcagcgcggc tatcgtggct ggccacgacg    4080
ggcgttcctt gcgcagctgt gctcgacgtt gtcactgaag cgggaaggga ctggctgcta    4140
ttgggcgaag tgccggggca ggatctcctg tcatctcacc ttgctcctgc cgagaaagta    4200
tccatcatgg ctgatgcaat gcggcggctg catacgcttg atccggctac ctgcccattc    4260
gaccaccaag cgaaacatcg catcgagcga gcacgtactc ggatggaagc cggtcttgtc    4320
gatcaggatg atctggacga agagcatcag gggctcgcgc cagccgaact gttcgccagg    4380
ctcaaggcgc gcatgcccga cggcgaggat ctcgtcgtga cccatggcga tgcctgcttg    4440
ccgaatatca tggtggaaaa tggccgcttt tctggattca tcgactgtgg ccggctgggt    4500
gtggcggacc gctatcagga catagcgttg gctacccgtg atattgctga agagcttggc    4560
```

```
ggcgaatggg ctgaccgctt cctcgtgctt tacggtatcg ccgctcccga ttcgcagcgc    4620
atcgccttct atcgccttct tgacgagttc ttctgagcgg gactctgggg ttcgaaatga    4680
ccgaccaagc gacgcccaac ctgccatcac gagatttcga ttccaccgcc gccttctatg    4740
aaaggttggg cttcggaatc gttttccggg acgccggctg gatgatcctc cagcgcgggg    4800
atctcatgct ggagttcttc gcccacccca acttgtttat tgcagcttat aatggttaca    4860
aataaagcaa tagcatcaca aatttcacaa ataaagcatt tttttcactg cattctagtt    4920
gtggtttgtc caaactcatc aatgtatctt atcatgtctg tataccgtcg acctctagct    4980
agagcttggc gtaatcatgg tcatagctgt ttcctgtgtg aaattgttat ccgctcacaa    5040
ttccacacaa catacgagcc ggaagcataa agtgtaaagc ctggggtgcc taatgagtga    5100
gctaactcac attaattgcg ttgcgctcac tgcccgcttt ccagtcggga aacctgtcgt    5160
gccagctgca ttaatgaatc ggccaacgcg cggggagagg cggtttgcgt attgggcgct    5220
cttccgcttc ctcgctcact gactcgctgc gctcggtcgt tcggctgcgg cgagcggtat    5280
cagctcactc aaaggcggta atacggttat ccacagaatc aggggataac gcaggaaaga    5340
acatgtgagc aaaaggccag caaaaggcca ggaaccgtaa aaaggccgcg ttgctggcgt    5400
ttttccatag gctccgcccc cctgacgagc atcacaaaaa tcgacgctca agtcagaggt    5460
ggcgaaaccc gacaggacta taaagatacc aggcgtttcc ccctggaagc tccctcgtgc    5520
gctctcctgt tccgaccctg ccgcttaccg gatacctgtc cgcctttctc ccttcgggaa    5580
gcgtggcgct ttctcatagc tcacgctgta ggtatctcag ttcggtgtag tcgttcgct    5640 ccaagctggg ctgtgtgcac gaaccccccg ttcagcccga ccgctgcgcc ttatccggta    5700
actatcgtct tgagtccaac ccggtaagac acgacttatc gccactggca gcagccactg    5760
gtaacaggat tagcagagcg aggtatgtag gcggtgctac agagttcttg aagtggtggc    5820
ctaactacgg ctacactaga agaacagtat ttggtatctg cgctctgctg aagccagtta    5880
ccttcggaaa aagagttggt agctcttgat ccggcaaaca aaccaccgct ggtagcggtt    5940
tttttgtttg caagcagcag attacgcgca gaaaaaaagg atctcaagaa gatcctttga    6000
tcttttctac ggggtctgac gctcagtgga acgaaaactc acgttaaggg attttggtca    6060
tgagattatc aaaaaggatc ttcacctaga tccttttaaa ttaaaaatga agttttaaat    6120
caatctaaag tatatatgag taaacttggt ctgacagtta ccaatgctta atcagtgagg    6180
cacctatctc agcgatctgt ctatttcgtt catccatagt tgcctgactc cccgtcgtgt    6240
agataactac gatacgggag ggcttaccat ctggccccag tgctgcaatg ataccgcgag    6300
acccacgctc accggctcca gatttatcag caataaacca gccagccgga agggccgagc    6360
gcagaagtgg tcctgcaact ttatccgcct ccatccagtc tattaattgt tgccgggaag    6420
ctagagtaag tagttcgcca gttaatagtt tgcgcaacgt tgttgccatt gctacaggca    6480
tcgtggtgtc acgctcgtcg tttggtatgg cttcattcag ctccggttcc caacgatcaa    6540
ggcgagttac atgatccccc atgttgtgca aaaaagcggt tagctccttc ggtcctccga    6600
tcgttgtcag aagtaagttg gccgcagtgt tatcactcat ggttatggca gcactgcata    6660
attctcttac tgtcatgcca tccgtaagat gcttttctgt gactggtgag tactcaacca    6720
agtcattctg agaatagtgt atgcggcgac cgagttgctc ttgcccggcg tcaatacggg    6780
ataataccgc gccacatagc agaactttaa aagtgctcat cattggaaaa cgttcttcgg    6840
ggcgaaaact ctcaaggatc ttaccgctgt tgagatccag ttcgatgtaa cccactcgtg    6900
```

| | |
|---|---|
| cacccaactg atcttcagca tctttactt tcaccagcgt ttctgggtga gcaaaaacag | 6960 |
| gaaggcaaaa tgccgcaaaa aagggaataa gggcgacacg gaaatgttga atactcatac | 7020 |
| tcttcctttt tcaatattat tgaagcattt atcagggtta ttgtctcatg agcggataca | 7080 |
| tatttgaatg tatttagaaa aataaacaaa taggggttcc gcgcacattt ccccgaaaag | 7140 |
| tgccacctga cgtc | 7154 |

```
<210> SEQ ID NO 5
<211> LENGTH: 6773
<212> TYPE: DNA
<213> ORGANISM: artificial sequence
<220> FEATURE:
<223> OTHER INFORMATION: plasmid FLAG-Arrestin beta 1
<220> FEATURE:
<221> NAME/KEY: polyA_signal
<222> LOCATION: (82)..(306)
<223> OTHER INFORMATION: BGH  polyA_signal
<220> FEATURE:
<221> NAME/KEY: gene
<222> LOCATION: (1190)..(1984)
<223> OTHER INFORMATION: Neomycin resistance gene_CDS
<220> FEATURE:
<221> NAME/KEY: gene
<222> LOCATION: (3486)..(4346)
<223> OTHER INFORMATION: Ampicillin resistance gene_CDS
<220> FEATURE:
<221> NAME/KEY: promoter
<222> LOCATION: (4714)..(5301)
<223> OTHER INFORMATION: CMV_promoter
<220> FEATURE:
<221> NAME/KEY: gene
<222> LOCATION: (5447)..(5476)
<223> OTHER INFORMATION: gene encoding the FLAG epitope_CDS
<220> FEATURE:
<221> NAME/KEY: gene
<222> LOCATION: (5507)..(6760)
<223> OTHER INFORMATION: gene encoding human beat-arrestin 1_CDS

<400> SEQUENCE: 5
```

| | |
|---|---|
| cttgtacaaa gtggtgatat ccagcacagt ggcggccgct cgagtctaga gggcccgttt | 60 |
| aaacccgctg atcagcctcg actgtgcctt ctagttgcca gccatctgtt gtttgcccct | 120 |
| cccccgtgcc ttccttgacc ctggaaggtg ccactcccac tgtcctttcc taataaaatg | 180 |
| aggaaattgc atcgcattgt ctgagtaggt gtcattctat tctggggggt ggggtggggc | 240 |
| aggacagcaa gggggaggat tgggaagaca atagcaggca tgctgggat gcggtgggct | 300 |
| ctatggcttc tgaggcggaa agaaccagct ggggctctag ggggtatccc cacgcgccct | 360 |
| gtagcggcgc attaagcgcg gcgggtgtgg tggttacgcg cagcgtgacc gctacacttg | 420 |
| ccagcgccct agcgcccgct cctttcgctt tcttcccttc ctttctcgcc acgttcgccg | 480 |
| gctttccccg tcaagctcta aatcgggggc tccctttagg gttccgattt agtgctttac | 540 |
| ggcacctcga ccccaaaaaa cttgattagg gtgatggttc acgtagtggg ccatcgccct | 600 |
| gatagacggt ttttcgccct ttgacgttgg agtccacgtt ctttaatagt ggactcttgt | 660 |
| tccaaactgg aacaacactc aaccctatct cggtctattc ttttgattta agggatt | 720 |
| tgccgatttc ggcctattgg ttaaaaaatg agctgattta caaaaatttt aacgcgaatt | 780 |
| aattctgtgg aatgtgtgtc agttagggtg tggaaagtcc ccaggctccc cagcaggcag | 840 |
| aagtatgcaa agcatgcatc tcaattagtc agcaaccagg tgtggaaagt ccccaggctc | 900 |
| cccagcaggc agaagtatgc aaagcatgca tctcaattag tcagcaacca tagtcccgcc | 960 |
| cctaactccg cccatcccgc cctaactccg cccagttccg cccattctc cgccccatgg | 1020 |
| ctgactaatt ttttttattt atgcagaggc cgaggccgcc tctgcctctg agctattcca | 1080 |

```
gaagtagtga ggaggctttt ttggaggcct aggcttttgc aaaaagctcc cgggagcttg    1140
tatatccatt ttcggatctg atcaagagac aggatgagga tcgtttcgca tgattgaaca    1200
agatggattg cacgcaggtt ctccggccgc ttgggtggag aggctattcg gctatgactg    1260
ggcacaacag acaatcggct gctctgatgc cgccgtgttc cggctgtcag cgcaggggcg    1320
cccggttctt tttgtcaaga ccgacctgtc cggtgccctg aatgaactgc aggacgaggc    1380
agcgcggcta tcgtggctgg ccacgacggg cgttccttgc gcagctgtgc tcgacgttgt    1440
cactgaagcg ggaagggact ggctgctatt gggcgaagtg ccggggcagg atctcctgtc    1500
atctcacctt gctcctgccg agaaagtatc catcatggct gatgcaatgc ggcggctgca    1560
tacgcttgat ccggctacct gcccattcga ccaccaagcg aaacatcgca tcgagcgagc    1620
acgtactcgg atggaagccg gtcttgtcga tcaggatgat ctggacgaag agcatcaggg    1680
gctcgcgcca gccgaactgt tcgccaggct caaggcgcgc atgcccgacg gcgaggatct    1740
cgtcgtgacc catggcgatg cctgcttgcc gaatatcatg gtggaaaatg gccgcttttc    1800
tggattcatc gactgtggcc ggctgggtgt ggcggaccgc tatcaggaca tagcgttggc    1860
tacccgtgat attgctgaag agcttggcgg cgaatgggct gaccgcttcc tcgtgcttta    1920
cggtatcgcc gctcccgatt cgcagcgcat cgccttctat cgccttcttg acgagttctt    1980
ctgagcggga ctctggggtt cgaaatgacc gaccaagcga cgcccaacct gccatcacga    2040
gatttcgatt ccaccgccgc cttctatgaa aggttgggct tcggaatcgt tttccgggac    2100
gccggctgga tgatcctcca gcgcggggat ctcatgctgg agttcttcgc ccaccccaac    2160
ttgtttattg cagcttataa tggttacaaa taaagcaata gcatcacaaa tttcacaaat    2220
aaagcatttt tttcactgca ttctagttgt ggtttgtcca aactcatcaa tgtatcttat    2280
catgtctgta taccgtcgac ctctagctag agcttggcgt aatcatggtc atagctgttt    2340
cctgtgtgaa attgttatcc gctcacaatt ccacacaaca tacgagccgg aagcataaag    2400
tgtaaagcct ggggtgccta atgagtgagc taactcacat taattgcgtt gcgctcactg    2460
cccgctttcc agtcgggaaa cctgtcgtgc cagctgcatt aatgaatcgg ccaacgcgcg    2520
gggagaggcg gtttgcgtat tgggcgctct tccgcttcct cgctcactga ctcgctgcgc    2580
tcggtcgttc ggctgcggcg agcggtatca gctcactcaa aggcggtaat acggttatcc    2640
acagaatcag gggataacgc aggaaagaac atgtgagcaa aaggccagca aaaggccagg    2700
aaccgtaaaa aggccgcgtt gctggcgttt ttccataggc tccgcccccc tgacgagcat    2760
cacaaaaatc gacgctcaag tcagaggtgg cgaaacccga caggactata agataccagg    2820
cgtttccccc tggaagctcc ctcgtgcgct ctcctgttcc gaccctgccg cttaccgga    2880 tacctgtccg cctttctccc ttcgggaagc gtggcgcttt ctcatagctc acgctgtagg    2940
tatctcagtt cggtgtaggt cgttcgctcc aagctgggct gtgtgcacga accccccgtt    3000
cagcccgacc gctgcgcctt atccggtaac tatcgtcttg agtccaaccc ggtaagacac    3060
gacttatcgc cactggcagc agccactggt aacaggatta gcagagcgag gtatgtaggc    3120
ggtgctacag agttcttgaa gtggtggcct aactacggct acactagaag aacagtattt    3180
ggtatctgcg ctctgctgaa gccagttacc ttcggaaaaa gagttggtag ctcttgatcc    3240
ggcaaacaaa ccaccgctgg tagcggtttt tttgtttgca agcagcagat tacgcgcaga    3300
aaaaaaggat ctcaagaaga tcctttgatc ttttctacgg ggtctgacgc tcagtggaac    3360
gaaaactcac gttaagggat tttggtcatg agattatcaa aaaggatctt cacctagatc    3420
```

```
cttttaaatt aaaaatgaag ttttaaatca atctaaagta tatatgagta aacttggtct    3480
gacagttacc aatgcttaat cagtgaggca cctatctcag cgatctgtct atttcgttca    3540
tccatagttg cctgactccc cgtcgtgtag ataactacga tacgggaggg cttaccatct    3600
ggccccagtg ctgcaatgat accgcgagac ccacgctcac cggctccaga tttatcagca    3660
ataaaccagc cagccggaag ggccgagcgc agaagtggtc ctgcaacttt atccgcctcc    3720
atccagtcta ttaattgttg ccgggaagct agagtaagta gttcgccagt taatagtttg    3780
cgcaacgttg ttgccattgc tacaggcatc gtggtgtcac gctcgtcgtt tggtatggct    3840
tcattcagct ccggttccca acgatcaagg cgagttacat gatcccccat gttgtgcaaa    3900
aaagcggtta gctccttcgg tcctccgatc gttgtcagaa gtaagttggc cgcagtgtta    3960
tcactcatgg ttatggcagc actgcataat tctcttactg tcatgccatc cgtaagatgc    4020
ttttctgtga ctggtgagta ctcaaccaag tcattctgag aatagtgtat gcggcgaccg    4080
agttgctctt gcccggcgtc aatacggggat aataccgcgc cacatagcag aactttaaaa    4140
gtgctcatca ttggaaaacg ttcttcgggg cgaaaactct caaggatctt accgctgttg    4200
agatccagtt cgatgtaacc cactcgtgca cccaactgat cttcagcatc ttttactttc    4260
accagcgttt ctgggtgagc aaaaacagga aggcaaaatg ccgcaaaaaa gggaataagg    4320
gcgacacgga aatgttgaat actcatactc ttccttttc aatattattg aagcatttat    4380
cagggttatt gtctcatgag cggatacata tttgaatgta tttagaaaaa taaacaaata    4440
ggggttccgc gcacatttcc ccgaaaagtg ccacctgacg tcgacggatc gggagatctc    4500
ccgatcccct atggtgcact ctcagtacaa tctgctctga tgccgcatag ttaagccagt    4560
atctgctccc tgcttgtgtg ttggaggtcg ctgagtagtg cgcgagcaaa atttaagcta    4620
caacaaggca aggcttgacc gacaattgca tgaagaatct gcttagggtt aggcgttttg    4680
cgctgcttcg cgatgtacgg gccagatata cgcgttgaca ttgattattg actagttatt    4740
aatagtaatc aattacgggg tcattagttc atagcccata tatggagttc cgcgttacat    4800
aacttacggt aaatggcccg cctggctgac cgcccaacga cccccgccca ttgacgtcaa    4860
taatgacgta tgttcccata gtaacgccaa tagggacttt ccattgacgt caatgggtgg    4920
agtatttacg gtaaactgcc cacttggcag tacatcaagt gtatcatatg ccaagtacgc    4980
cccctattga cgtcaatgac ggtaaatggc ccgcctggca ttatgcccag tacatgacct    5040
tatgggactt tcctacttgg cagtacatct acgtattagt catcgctatt accatggtga    5100
tgcggttttg gcagtacatc aatgggcgtg atagcggtt tgactcacgg ggatttccaa    5160
gtctccaccc cattgacgtc aatgggagtt tgttttggca ccaaaatcaa cgggactttc    5220
caaaatgtcg taacaactcc gccccattga cgcaaatggg cggtaggcgt gtacggtggg    5280
aggtctatat aagcagagct ctctggctaa ctagagaacc cactgcttac tggcttatcg    5340
aaattaatac gactcactat agggagaccc aagctggcta gcgtttaaac ttaagcttgg    5400
taccgagctc ggatccacta gtccagtgtg gtggaattct gcagatatgg actcaaagga    5460
cgacgacgac aaggatatca caagtttgta caaaaaagca ggcaccatgg cgacaaagg    5520 gacccgagtg ttcaagaagg ccagtccaaa tggaaagctc accgtctacc tgggaaagcg    5580
ggactttgtg gaccacatcg acctcgtgga ccctgtggat ggtgtggtcc tggtggatcc    5640
tgagtatctc aaagagcgga gagtctatgt gacgctgacc tgcgccttcc gctatggccg    5700
ggaggacctg gatgtcctgg gcctgacctt tcgcaaggac ctgtttgtgg ccaacgtaca    5760
gtcgttccca ccggcccccg aggacaagaa gccccctgacg cggctgcagg aacgcctcat    5820
```

```
caagaagctg ggcgagcacg cttacccttt caccttttgag atccctccaa accttccatg    5880
ttctgtgaca ctgcagccgg ggcccgaaga cacggggaag gcttgcggtg tggactatga    5940
agtcaaagcc ttctgcgcgg agaatttgga ggagaagatc cacaagcgga attctgtgcg    6000
tctggtcatc cggaaggttc agtatgcccc agagaggcct ggcccccagc ccacagccga    6060
gaccaccagg cagttcctca tgtcggacaa gcccttgcac ctagaagcct ctctggataa    6120
ggagatctat taccatggag aacccatcag cgtcaacgtc cacgtcacca acaacaccaa    6180
caagacggtg aagaagatca agatctcagt gcgccagtat gcagacatct gccttttcaa    6240
cacagctcag tacaagtgcc ctgttgccat ggaagaggct gatgacactg tggcacccag    6300
ctcgacgttc tgcaaggtct acacactgac ccccttccta gccaataacc gagagaagcg    6360
gggcctcgcc ttggacggga agctcaagca cgaagcacg aacttggcct ctagcaccct    6420
gttgagggaa ggtgccaacc gtgagatcct ggggatcatt gtttcctaca aagtgaaagt    6480
gaagctggtg gtgtctcggg gcggcctgtt gggagatctt gcatccagcg acgtggccgt    6540
ggaactgccc ttcacccta tgcaccccaa gcccaaagag gaaccccgc atcgggaagt    6600 tccagagaac gagacgccag tagataccaa tctcatagaa cttgacacaa atgatgacga    6660
cattgtattt gaggactttg ctcgccagag actgaaaggc atgaaggatg acaaggagga    6720
agaggaggat ggtaccggct ctccacagct caacaacaga tagacccagc ttt           6773
```

<210> SEQ ID NO 6
<211> LENGTH: 7130
<212> TYPE: DNA
<213> ORGANISM: artificial sequence
<220> FEATURE:
<223> OTHER INFORMATION: plasmid FLAG-ST-CXCR7
<220> FEATURE:
<221> NAME/KEY: promoter
<222> LOCATION: (232)..(819)
<223> OTHER INFORMATION: CMV_promoter
<220> FEATURE:
<221> NAME/KEY: sig_peptide
<222> LOCATION: (923)..(986)
<223> OTHER INFORMATION: T8 signal peptide
<220> FEATURE:
<221> NAME/KEY: gene
<222> LOCATION: (1004)..(1027)
<223> OTHER INFORMATION: gene encoding the FLAG epitope_CDS
<220> FEATURE:
<221> NAME/KEY: gene
<222> LOCATION: (1046)..(1591)
<223> OTHER INFORMATION: gene encoding the Snap Tag enzyme_CDS
<220> FEATURE:
<221> NAME/KEY: gene
<222> LOCATION: (1595)..(2687)
<223> OTHER INFORMATION: gene encoding the CXCR7 receptor_CDS
<220> FEATURE:
<221> NAME/KEY: polyA_signal
<222> LOCATION: (2730)..(2954)
<223> OTHER INFORMATION: BGH polyA_signal
<220> FEATURE:
<221> NAME/KEY: gene
<222> LOCATION: (3838)..(4632)
<223> OTHER INFORMATION: Neomycin resistance gene_CDS
<220> FEATURE:
<221> NAME/KEY: gene
<222> LOCATION: (6134)..(6994)
<223> OTHER INFORMATION: Ampicillin resistance gene_CDS

<400> SEQUENCE: 6

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
```

```
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacgggtc attagttcat agcccatata       300
tggagttccg cgttacataa cttacggtaa atggcccgcc tggctgaccg cccaacgacc      360
cccgcccatt gacgtcaata atgacgtatg ttcccatagt aacgccaata gggactttcc     420
attgacgtca atgggtggag tatttacggt aaactgccca cttggcagta catcaagtgt      480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc     900
gtttaaactt aagctttgag acatggcctt accagtgacc gccttgctcc tgccgctggc    960
cttgctgctc cacgccgcca ggccggccgc cgctagcggc atcgactaca aggacgacga    1020
tgacaaggcc ggcatcgatg ccatcatgga caaagactgc gaaatgaagc gcaccaccct    1080
ggatagccct ctgggcaagc tggaactgtc tgggtgcgaa cagggcctgc acgagatcaa    1140
gctgctgggc aaaggaacat ctgccgccga cgccgtggaa gtgcctgccc agccgccgt    1200 gctgggcgga ccagagccac tgatgcaggc caccgcctgg ctcaacgcct actttcacca    1260
gcctgaggcc atcgaggagt ccctgtgtcc agccctgcac cacccagtgt ccagcagga    1320 gagctttacc cgccaggtgc tgtggaaact gctgaaagtg gtgaagttcg gagaggtcat    1380
cagctaccag cagctggccg ccctggccgg caatcccgcc gccaccgccg ccgtgaaaac    1440
cgccctgagc ggaaatcccg tgcccattct gatccctgc accgggtgg tgtctagctc     1500 tggcgccgtg gggggctacg agggcgggct cgccgtgaaa gagtggctgc tggcccacga    1560
gggccacaga ctgggcaagc ctgggctggg tgatatcctg gatctgcatc tcttcgacta    1620
ctcagagcca gggaacttct cggacatcag ctggccatgc aacagcagcg actgcatcgt    1680
ggtggacacg gtgatgtgtc caacatgcc caacaaaagc gtcctgctct acacgctctc    1740
cttcatttac attttcatct tcgtcatcgg catgattgcc aactccgtgg tggtctgggt    1800
gaatatccag gccaagacca caggctatga cacgcactgc tacatcttga acctggccat    1860
tgccgacctg tgggttgtcc tcaccatccc agtctgggtg gtcagtctcg tgcagcacaa    1920
ccagtggccc atgggcgagc tcacgtgcaa agtcacacac ctcatcttct ccatcaacct    1980
cttcagcagc atttttcttc ctcacgtgcat gagcgtggac cgctacctct ccatcaccta    2040
cttcaccaac accccagca gcaggaagaa gatggtacgc cgtgtcgtct gcatcctggt    2100
gtggctgctg gccttctgcg tgtctctgcc tgacacctac tacctgaaga ccgtcacgtc    2160
tgcgtccaac aatgagacct actgccggtc cttctacccc gagcacagca tcaaggagtg    2220
gctgatcggc atggagctgg tctccgttgt cttgggcttt gccgttccct tctccattat    2280
cgctgtcttc tacttcctgc tggccagagc catctcggcg tccagtgacc aggagaagca    2340
cagcagccgg aagatcatct ctcctacgt ggtggtcttc cttgtctgct ggttgcccta    2400
ccacgtggcg gtgctgctgg acatcttctc catcctgcac tacatccctt tcacctgccg    2460
gctggagcac gccctcttca cggccctgca tgtcacacag tgcctgtcgc tggtgcactg    2520
```

```
ctgcgtcaac cctgtcctct acagcttcat caatcgcaac tacaggtacg agctgatgaa    2580
ggccttcatc ttcaagtact cggccaaaac agggctcacc aagctcatcg atgcctccag    2640
agtctcagag acggagtact ctgccttgga gcagagcacc aaatgactcg agtctagagg    2700
gcccgtttaa acccgctgat cagcctcgac tgtgccttct agttgccagc catctgttgt    2760
ttgcccctcc cccgtgcctt ccttgaccct ggaaggtgcc actcccactg tcctttccta    2820
ataaaatgag gaaattgcat cgcattgtct gagtaggtgt cattctattc tggggggtgg    2880
ggtggggcag gacagcaagg gggaggattg ggaagacaat agcaggcatg ctggggatgc    2940
ggtgggctct atggcttctg aggcggaaag aaccagctgg ggctctaggg ggtatcccca    3000
cgcgccctgt agcggcgcat taagcgcggc gggtgtggtg gttacgcgca gcgtgaccgc    3060
tacacttgcc agcgccctag cgcccgctcc tttcgctttc ttcccttcct ttctcgccac    3120
gttcgccggc tttccccgtc aagctctaaa tcggggctc cctttagggt tccgatttag    3180
tgctttacgg cacctcgacc ccaaaaaact tgattaggt gatggttcac gtagtgggcc    3240
atcgccctga tagacggttt ttcgcccttt gacgttggag tccacgttct ttaatagtgg    3300
actcttgttc caaactggaa caacactcaa ccctatctcg gtctattctt ttgatttata    3360
agggattttg ccgatttcgg cctattggtt aaaaaatgag ctgatttaac aaaaatttaa    3420
cgcgaattaa ttctgtggaa tgtgtgtcag ttagggtgtg gaaagtcccc aggctcccca    3480
gcaggcagaa gtatgcaaag catgcatctc aattagtcag caaccaggtg tggaaagtcc    3540
ccaggctccc cagcaggcag aagtatgcaa agcatgcatc tcaattagtc agcaaccata    3600
gtcccgcccc taactccgcc catcccgccc ctaactccgc ccagttccgc ccattctccg    3660
ccccatggct gactaatttt ttttatttat gcagaggccg aggccgcctc tgcctctgag    3720
ctattccaga agtagtgagg aggcttttt ggaggcctag gcttttgcaa aaagctcccg    3780
ggagcttgta tatccatttt cggatctgat caagagacag gatgaggatc gtttcgcatg    3840
attgaacaag atggattgca cgcaggttct ccggccgctt gggtggagag gctattcggc    3900
tatgactggg cacaacagac aatcggctgc tctgatgccg ccgtgttccg gctgtcagcg    3960
caggggcgcc cggttctttt tgtcaagacc gacctgtccg gtgccctgaa tgaactgcag    4020
gacgaggcag cgcggctatc gtggctggcc acgacgggcg ttccttgcgc agctgtgctc    4080
gacgttgtca ctgaagcggg aagggactgg ctgctattgg gcgaagtgcc ggggcaggat    4140
ctcctgtcat ctcaccttgc tcctgccgag aaagtatcca tcatggctga tgcaatgcgg    4200
cggctgcata cgcttgatcc ggctacctgc ccattcgacc accaagcgaa acatcgcatc    4260
gagcgagcac gtactcggat ggaagccggt cttgtcgatc aggatgatct ggacgaagag    4320 catcagggc tcgcgccagc cgaactgttc gccaggctca aggcgcgcat gcccgacggc    4380
gaggatctcg tcgtgaccca tggcgatgcc tgcttgccga atatcatggt ggaaaatggc    4440
cgcttttctg gattcatcga ctgtggccgg ctgggtgtgg cggaccgcta tcaggacata    4500
gcgttggcta cccgtgatat tgctgaagag cttggcggcg aatgggctga ccgcttcctc    4560
gtgctttacg gtatcgccgc tcccgattcg cagcgcatcg ccttctatcg ccttcttgac    4620
gagttcttct gagcgggact ctggggttcg aaatgaccga ccaagcgacg cccaacctgc    4680
catcacgaga tttcgattcc accgccgcct tctatgaaag gttgggcttc ggaatcgttt    4740
tccgggacgc cggctggatg atcctccagc gcggggatct catgctggag ttcttcgccc    4800
accccaactt gtttattgca gcttataatg gttacaaata aagcaatagc atcacaaatt    4860
```

```
tcacaaataa agcattttttt tcactgcatt ctagttgtgg tttgtccaaa ctcatcaatg      4920
tatcttatca tgtctgtata ccgtcgacct ctagctagag cttggcgtaa tcatggtcat      4980
agctgttttcc tgtgtgaaat tgttatccgc tcacaattcc acacaacata cgagccggaa     5040
gcataaagtg taaagcctgg ggtgcctaat gagtgagcta actcacatta attgcgttgc      5100
gctcactgcc cgctttccag tcgggaaacc tgtcgtgcca gctgcattaa tgaatcggcc      5160
aacgcgcggg gagaggcggt ttgcgtattg ggcgctcttc cgcttcctcg ctcactgact      5220
cgctgcgctc ggtcgttcgg ctgcggcgag cggtatcagc tcactcaaag gcggtaatac      5280
ggttatccac agaatcaggg gataacgcag gaaagaacat gtgagcaaaa ggccagcaaa      5340
aggccaggaa ccgtaaaaag gccgcgttgc tggcgttttt ccataggctc cgcccccctg      5400
acgagcatca caaaaatcga cgctcaagtc agaggtggcg aaacccgaca ggactataaa      5460
gataccaggc gtttccccct ggaagctccc tcgtgcgctc tcctgttccg accctgccgc      5520
ttaccggata cctgtccgcc tttctccctt cgggaagcgt ggcgctttct catagctcac      5580
gctgtaggta tctcagttcg gtgtaggtcg ttcgctccaa gctgggctgt gtgcacgaac      5640
cccccgttca gcccgaccgc tgcgccttat ccggtaacta tcgtcttgag tccaacccgg      5700
taagacacga cttatcgcca ctggcagcag ccactggtaa caggattagc agagcgaggt      5760
atgtaggcgg tgctacagag ttcttgaagt ggtggcctaa ctacggctac actagaagaa      5820
cagtatttgg tatctgcgct ctgctgaagc cagttacctt cggaaaaaga gttggtagct      5880
cttgatccgg caaacaaacc accgctggta gcggtttttt tgtttgcaag cagcagatta      5940
cgcgcagaaa aaaaggatct caagaagatc ctttgatctt ttctacgggg tctgacgctc      6000
agtggaacga aaactcacgt taagggattt tggtcatgag attatcaaaa aggatcttca      6060
cctagatcct tttaaattaa aaatgaagtt ttaaatcaat ctaaagtata tatgagtaaa      6120
cttggtctga cagttaccaa tgcttaatca gtgaggcacc tatctcagcg atctgtctat      6180
ttcgttcatc catagttgcc tgactccccg tcgtgtagat aactacgata cgggagggct      6240
taccatctgg ccccagtgct gcaatgatac cgcgagaccc acgctcaccg gctccagatt      6300
tatcagcaat aaaccagcca gccggaaggg ccgagcgcag aagtggtcct gcaactttat      6360
ccgcctccat ccagtctatt aattgttgcc gggaagctag agtaagtagt tcgccagtta      6420
atagtttgcg caacgttgtt gccattgcta caggcatcgt ggtgtcacgc tcgtcgtttg      6480
gtatggcttc attcagctcc ggttcccaac gatcaaggcg agttacatga tcccccatgt      6540
tgtgcaaaaa agcggttagc tccttcggtc ctccgatcgt tgtcagaagt aagttggccg      6600
cagtgttatc actcatggtt atggcagcac tgcataattc tcttactgtc atgccatccg      6660
taagatgctt ttctgtgact ggtgagtact caaccaagtc attctgagaa tagtgtatgc      6720
ggcgaccgag ttgctcttgc ccggcgtcaa tacgggataa taccgcgcca catagcagaa      6780
ctttaaaagt gctcatcatt ggaaaacgtt cttcggggcg aaaactctca aggatcttac      6840
cgctgttgag atccagttcg atgtaaccca ctcgtgcacc caactgatct tcagcatctt      6900
ttactttcac cagcgtttct gggtgagcaa aaacaggaag gcaaaatgcc gcaaaaaagg      6960
gaataagggc gacacggaaa tgttaatac tcatactctt cctttttcaa tattattgaa       7020
gcatttatca gggttattgt ctcatgagcg gatacatatt tgaatgtatt tagaaaaata     7080
aacaaatagg ggttccgcgc acatttcccc gaaaagtgcc acctgacgtc              7130
```

<210> SEQ ID NO 7
<211> LENGTH: 7295

```
<212> TYPE: DNA
<213> ORGANISM: artificial sequence
<220> FEATURE:
<223> OTHER INFORMATION: plasmid FLAG-ST-Beta 2AR
<220> FEATURE:
<221> NAME/KEY: promoter
<222> LOCATION: (232)..(819)
<223> OTHER INFORMATION: CMV_promoter
<220> FEATURE:
<221> NAME/KEY: sig_peptide
<222> LOCATION: (923)..(986)
<223> OTHER INFORMATION: T8 signal peptide
<220> FEATURE:
<221> NAME/KEY: gene
<222> LOCATION: (1004)..(1027)
<223> OTHER INFORMATION: gene encoding the FLAG epitope_CDS
<220> FEATURE:
<221> NAME/KEY: gene
<222> LOCATION: (1046)..(1591)
<223> OTHER INFORMATION: gene encoding the Snap Tag enzyme_CDS
<220> FEATURE:
<221> NAME/KEY: gene
<222> LOCATION: (1622)..(2857)
<223> OTHER INFORMATION: gene encoding the beta 2AR_CDS
<220> FEATURE:
<221> NAME/KEY: polyA_signal
<222> LOCATION: (2895)..(3119)
<223> OTHER INFORMATION: BGH polyA_signal
<220> FEATURE:
<221> NAME/KEY: gene
<222> LOCATION: (4003)..(4797)
<223> OTHER INFORMATION: Neomycin resistance gene_CDS
<220> FEATURE:
<221> NAME/KEY: gene
<222> LOCATION: (6299)..(7159)
<223> OTHER INFORMATION: Ampicillin resistance gene_CDS

<400> SEQUENCE: 7
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctttgag acatggcctt accagtgacc gccttgctcc tgccgctggc     960
cttgctgctc cacgccgcca ggccggccgc cgctagcgga atcgactaca aggacgacga    1020
tgacaaggcc ggcatcgatg ccatcatgga caaagactgc gaaatgaagc gcaccaccct    1080
ggatagccct ctgggcaagc tggaactgtc tgggtgcgaa cagggcctgc acgagatcaa    1140
gctgctgggc aaaggaacat ctgccgccga cgccgtggaa gtgcctgccc cagccgccgt    1200
```

```
gctgggcgga ccagagccac tgatgcaggc caccgcctgg ctcaacgcct actttcacca    1260
gcctgaggcc atcgaggagt tccctgtgcc agccctgcac cacccagtgt tccagcagga    1320
gagctttacc cgccaggtgc tgtggaaact gctgaaagtg gtgaagttcg agaggtcat     1380 cagctaccag cagctggccg ccctggccgg caatcccgcc gccaccgccg ccgtgaaaac    1440
cgccctgagc ggaaatcccg tgcccattct gatcccctgc caccgggtgg tgtctagctc    1500
tggcgccgtg gggggctacg agggcgggct cgccgtgaaa gagtggctgc tggcccacga    1560
gggccacaga ctgggcaagc ctgggctggg tgatatccag cacagtggcg ccgctcgag     1620 agggcaaccc gggaacggca gcgccttctt gctggcaccc aatagaagcc atgcgccgga    1680
ccacgacgtc acgcagcaaa gggacgaggt gtgggtggtg ggcatgggca tcgtcatgtc    1740
tctcatcgtc ctggccatcg tgtttggcaa tgtgctggtc atcacagcca ttgccaagtt    1800
cgagcgtctg cagacggtca ccaactactt catcacttca ctggcctgtg ctgatctggt    1860
catgggcctg gcagtggtgc cctttggggc cgcccatatt cttatgaaaa tgtggacttt    1920
tggcaacttc tggtgcgagt tttggactc cattgatgtg ctgtgcgtca cggccagcat     1980
tgagaccctg tgcgtgatcg cagtggatcg ctactttgcc attacttcac ctttcaagta    2040
ccagagcctg ctgaccaaga ataaggcccg ggtgatcatt ctgatggtgt ggattgtgtc    2100
aggccttacc tccttcttgc ccattcagat gcactggtac cgggccaccc accaggaagc    2160
catcaactgc tatgccaatg agacctgctg tgacttcttc acgaaccaag cctatgccat    2220
tgcctcttcc atcgtgtcct tctacgttcc cctggtgatc atggtcttcg tctactccag    2280
ggtctttcag gaggccaaaa ggcagctcca gaagattgac aaatctgagg ccgcttcca    2340 tgtccagaac cttagccagg tggagcagga tgggcggacg gggcatggac tccgcagatc    2400
ttccaagttc tgcttgaagg agcacaaagc cctcaagacg ttaggcatca tcatgggcac    2460 tttcacccctc tgctggctgc ccttcttcat cgttaacatt gtgcatgtga tccaggataa    2520
cctcatccgt aaggaagttt acatcctcct aaattggata ggctatgtca attctggttt    2580
caatcccctt atctactgcc ggagcccaga tttcaggatt gccttccagg agcttctgtg    2640
cctgcgcagg tcttctttga aggcctatgg gaatggctac tccagcaacg gcaacacagg    2700
ggagcagagt ggatatcacg tggaacagga gaagaaaat aaactgctgt gtgaagacct    2760
cccaggcacg gaagactttg tgggccatca aggtactgtg cctagcgata acattgattc    2820
acaagggagg aattgtagta caatgactc actgctgtct agagggcccg tttaaacccg    2880
ctgatcagcc tcgactgtgc cttctagttg ccagccatct gttgtttgcc cctcccccgt    2940
gccttccttg acccctggaag gtgccactcc cactgtcctt tcctaataaa atgaggaaat    3000
tgcatcgcat tgtctgagta ggtgtcattc tattctgggg gtgggtgg ggcaggacag    3060 caagggggag gattgggaag acaatagcag gcatgctggg gatgcggtgg gctctatggc    3120
ttctgaggcg gaaagaacca gctgggctc taggggtat ccccacgcgc cctgtagcgg    3180
cgcattaagc gcggcgggtg tggtggttac gcgcagcgtg accgctacac ttgccagcgc    3240
cctagcgccc gctcctttcg ctttcttccc ttcctttctc gccacgttcg ccggctttcc    3300
ccgtcaagct ctaaatcggg ggctcccttt agggttccga tttagtgctt tacgcacct    3360 cgaccccaaa aaacttgatt agggtgatgg ttcacgtagt gggccatcgc cctgatagac    3420
ggtttttcgc cctttgacgt tggagtccac gttctttaat agtggactct tgttccaaac    3480
tggaacaaca ctcaaccctat ctcggtcta ttcttttgat ttataaggga ttttgccgat    3540
ttcggcctat tggttaaaaa atgagctgat ttaacaaaaa tttaacgcga attaattctg    3600
```

```
tggaatgtgt gtcagttagg gtgtggaaag tccccaggct ccccagcagg cagaagtatg    3660
caaagcatgc atctcaatta gtcagcaacc aggtgtggaa agtccccagg ctccccagca    3720
ggcagaagta tgcaaagcat gcatctcaat tagtcagcaa ccatagtccc gcccctaact    3780
ccgcccatcc cgcccctaac tccgcccagt tccgcccatt ctccgcccca tggctgacta    3840 attttttta tttatgcaga ggccgaggcc gcctctgcct ctgagctatt ccagaagtag    3900
tgaggaggct tttttggagg cctaggcttt tgcaaaaagc tcccgggagc ttgtatatcc    3960
attttcggat ctgatcaaga gacaggatga ggatcgtttc gcatgattga acaagatgga    4020
ttgcacgcag gttctccggc cgcttgggtg gagaggctat tcggctatga ctgggcacaa    4080
cagacaatcg gctgctctga tgccgccgtg ttccggctgt cagcgcaggg gcgcccggtt    4140 cttttgtca agaccgacct gtccggtgcc ctgaatgaac tgcaggacga ggcagcgcgg    4200
ctatcgtggc tggccacgac gggcgttcct tgcgcagctg tgctcgacgt tgtcactgaa    4260
gcgggaaggg actggctgct attgggcgaa gtgccggggc aggatctcct gtcatctcac    4320
cttgctcctg ccgagaaagt atccatcatg gctgatgcaa tgcggcggct gcatacgctt    4380
gatccggcta cctgcccatt cgaccaccaa gcgaaacatc gcatcgagcg agcacgtact    4440
cggatggaag ccggtcttgt cgatcaggat gatctggacg aagagcatca ggggctcgcg    4500
ccagccgaac tgttcgccag gctcaaggcg cgcatgcccg acggcgagga tctcgtcgtg    4560
acccatggcg atgcctgctt gccgaatatc atggtggaaa atggccgctt ttctggattc    4620
atcgactgtg gccggctggg tgtggcggac cgctatcagg acatagcgtt ggctacccgt    4680
gatattgctg aagagcttgg cggcgaatgg gctgaccgct tcctcgtgct ttacggtatc    4740
gccgctcccg attcgcagcg catcgccttc tatcgccttc ttgacgagtt cttctgagcg    4800
ggactctggg gttcgaaatg accgaccaag cgacgcccaa cctgccatca cgagatttcg    4860
attccaccgc cgccttctat gaaaggttgg gcttcggaat cgttttccgg gacgccggct    4920
ggatgatcct ccagcgcggg gatctcatgc tggagttctt cgcccacccc aacttgttta    4980
ttgcagctta taatggttac aaataaagca atagcatcac aaatttcaca ataaagcat    5040 tttttcact gcattctagt tgtggtttgt ccaaactcat caatgtatct tatcatgtct    5100
gtataccgtc gacctctagc tagagcttgg cgtaatcatg gtcatagctg tttcctgtgt    5160
gaaattgtta tccgctcaca attccacaca acatacgagc cggaagcata agtgtaaag    5220 cctggggtgc ctaatgagtg agctaactca cattaattgc gttgcgctca ctgcccgctt    5280
tccagtcggg aaacctgtcg tgccagctgc attaatgaat cggccaacgc gcggggagag    5340
gcggtttgcg tattgggcgc tcttccgctt cctcgctcac tgactcgctg cgctcggtcg    5400
ttcggctgcg gcgagcggta tcagctcact caaaggcggt aatacggtta tccacagaat    5460
caggggataa cgcaggaaag aacatgtgag caaaaggcca gcaaaggcc aggaaccgta    5520 aaaaggccgc gttgctggcg ttttccata ggctccgccc cctgacgag catcacaaaa    5580 atcgacgctc aagtcagagg tggcgaaacc cgacaggact ataaagatac caggcgtttc    5640
cccctggaag ctccctcgtg cgctctcctg ttccgaccct gccgcttacc ggatacctgt    5700
ccgcctttct cccttcggga agcgtggcgc tttctcatag ctcacgctgt aggtatctca    5760
gttcggtgta ggtcgttcgc tccaagctgg gctgtgtgca cgaaccccc gttcagcccg    5820 accgctgcgc cttatccggt aactatcgt ttgagtccaa cccggtaaga cacgacttat    5880
cgccactggc agcagccact ggtaacagga ttagcagagc gaggtatgta ggcggtgcta    5940
```

```
cagagttctt gaagtggtgg cctaactacg gctacactag aagaacagta tttggtatct      6000
gcgctctgct gaagccagtt accttcggaa aaagagttgg tagctcttga tccggcaaac      6060
aaaccaccgc tggtagcggt ttttttgttt gcaagcagca gattacgcgc agaaaaaaag      6120
gatctcaaga agatcctttg atcttttcta cggggtctga cgctcagtgg aacgaaaact      6180
cacgttaagg gattttggtc atgagattat caaaaaggat cttcacctag atccttttaa      6240
attaaaaatg aagttttaaa tcaatctaaa gtatatatga gtaaacttgg tctgacagtt      6300
accaatgctt aatcagtgag gcacctatct cagcgatctg tctatttcgt tcatccatag      6360
ttgcctgact ccccgtcgtg tagataacta cgatacggga gggcttacca tctggcccca      6420
gtgctgcaat gataccgcga gacccacgct caccggctcc agatttatca gcaataaacc      6480
agccagccgg aagggccgag cgcagaagtg gtcctgcaac tttatccgcc tccatccagt      6540
ctattaattg ttgccgggaa gctagagtaa gtagttcgcc agttaatagt ttgcgcaacg      6600
ttgttgccat tgctacaggc atcgtggtgt cacgctcgtc gtttggtatg gcttcattca      6660
gctccggttc ccaacgatca aggcgagtta catgatcccc catgttgtgc aaaaaagcgg      6720
ttagctcctt cggtcctccg atcgttgtca gaagtaagtt ggccgcagtg ttatcactca      6780
tggttatggc agcactgcat aattctctta ctgtcatgcc atccgtaaga tgcttttctg      6840
tgactggtga gtactcaacc aagtcattct gagaatagtg tatgcggcga ccgagttgct      6900
cttgcccggc gtcaatacgg gataataccg cgccacatag cagaacttta aaagtgctca      6960
tcattggaaa acgttcttcg gggcgaaaac tctcaaggat cttaccgctg ttgagatcca      7020
gttcgatgta acccactcgt gcacccaact gatcttcagc atcttttact ttcaccagcg      7080
tttctgggtg agcaaaaaca ggaaggcaaa atgccgcaaa aaagggaata agggcgacac      7140
ggaaatgttg aatactcata ctcttccttt tcaatatta ttgaagcatt tatcagggtt      7200
attgtctcat gagcggatac atatttgaat gtatttagaa aaataaacaa ataggggttc      7260
cgcgcacatt tccccgaaaa gtgccacctg acgtc                                 7295
```